United States Patent [19]

Foster et al.

[11] Patent Number: 5,200,340
[45] Date of Patent: Apr. 6, 1993

[54] THROMBIN-ACTIVATED TISSUE PLASMINOGEN ACTIVATORS

[75] Inventors: Donald C. Foster; Eileen R. Mulvihill; Patrick J. O'Hara, all of Seattle, Wash.; Kurt Pingel, Farum, Denmark; Shinji Yoshitake, Ibaraki, Japan

[73] Assignee: ZymoGenetics, Inc., Seattle, Wash.

[21] Appl. No.: 53,412

[22] Filed: May 22, 1987

[51] Int. Cl.$^5$ .................. C12N 9/61; C12N 15/00; C12N 15/58; C12N 15/35
[52] U.S. Cl. .................. 424/94.64; 435/212; 435/320.1; 435/240.2; 435/252.3; 435/252.33; 435/226; 536/23.2
[58] Field of Search ............ 435/212, 226, 320, 240.2, 435/252.3, 252.33, 320.1; 536/27; 424/94.64

[56] References Cited

FOREIGN PATENT DOCUMENTS 2173804A 10/1988 United Kingdom .

OTHER PUBLICATIONS

Tate et al. Biochemistry vol. 26: 338–343 (1987).
Stryer, Biochemistry, 1981, p. 105, 2nd Edition, Freeman & Co., San Francisco, U.S.A.
Lijnen, et al., *Eur. J. Biochem*, vol. 169, p. 359–364, 1987.
Ichinose et al., *J. Biol. Chem.*, vol. 261, p. 3486–3489, 1986.

*Primary Examiner*—Richard A. Schwartz
*Assistant Examiner*—Nancy Treptow
*Attorney, Agent, or Firm*—Seed and Berry

[57] ABSTRACT

Zymogens of proteins having fibrinolytic activity are disclosed. The proteins are cleavable by thrombin, the cleavage resulting in the stimulation of fibrinolytic activity. Suitable proteins which may be modified in accordance with the present invention include tissue plasminogen activator, urokinase, and plasminogen variants. The modified molecules are substantially clot-specific, in view of the large amounts of thrombin associated with clots in vivo.

11 Claims, 20 Drawing Sheets

FIG. 1A

```
                 10                          30                        45
AAGCTTGGAT CCACC ATG GAT GCA ATG AAG AGA GGG CTC TGC TGT GTG CTG CTG CTG
                 MET Asp Ala MET Lys Arg Gly Leu Cys Cys Val Leu Leu Leu
                 -35                     -30
      60                  75                     90                   105
TGT GGC GCC GTC TTC GTT TCG CCC AGC CAG GAA ATC CAT GCC CGA TTC AGA AGA
Cys Gly Ala Val Phe Val Ser Pro Ser Gln Glu Ile His Ala Arg Phe Arg Arg
    -20                                          -10
             120                 135                 150               165
GGA GCC AGA TCT TAC CAA GTG ATC TGC AGA GAT GAA AAA ACG CAG ATG ATA TAC
Gly Ala Arg Ser Tyr Gln Val Ile Cys Arg Asp Glu Lys Thr Gln MET Ile Tyr
            1                                    10
             180                 195                 210
CAG CAA CAT CAG TCA TGG CTG CGC CCT GTG CTC AGA AGC AAC CGG GTG GAA TAT
Gln Gln His Gln Ser Trp Leu Arg Pro Val Leu Arg Ser Asn Arg Val Glu Tyr
                  20                                  30
       225                 240                 255                 270
TGC TGG TGC AAC AGT GGC AGG GCA CAG TGC CAC TCA GTG CCT GTC AAA AGT TGC
Cys Trp Cys Asn Ser Gly Arg Ala Gln Cys His Ser Val Pro Val Lys Ser Cys
                         40                                        50
             285                 300                 315
AGC GAG CCA AGG TGT TTC AAC GGG GGC ACC TGC CAG CAG GCC CTG TAC TTC TCA
Ser Glu Pro Arg Cys Phe Asn Gly Gly Thr Cys Gln Gln Ala Leu Tyr Phe Ser
                                 60
 330                  345                 360                  375
GAT TTC GTG TGC CAG TGC CCC GAA GGA TTT GCT GGG AAG TGC TGT GAA ATA GAT
Asp Phe Val Cys Gln Cys Pro Glu Gly Phe Ala Gly Lys Cys Cys Glu Ile Asp
 70                                       80
             390                 405                 420                435
ACC AGG GCC ACG TGC TAC GAG GAC CAG GGC ATC AGC TAC AGG GGC ACG TGG AGC
Thr Arg Ala Thr Cys Tyr Glu Asp Gln Gly Ile Ser Tyr Arg Gly Thr Trp Ser
             90                                       100
             450                 465                 480
ACA GCG GAG AGT GGC GCC GAG TGC ACC AAC TGG AAC AGC AGC GCG TTG GCC CAG
Thr Ala Glu Ser Gly Ala Glu Cys Thr Asn Trp Asn Ser Ser Ala Leu Ala Gln
             110                                     120
       495                 510                 525                 540
AAG CCC TAC AGC GGG CGG AGG CCA GAC GCC ATC AGG CTG GGC CTG GGG AAC CAC
Lys Pro Tyr Ser Gly Arg Arg Pro Asp Ala Ile Arg Leu Gly Leu Gly Asn His
                         130                                       140
             555                 570                 585
AAC TAC TGC AGA AAC CCA GAT CGA GAC TCA AAG CCC TGG TGC TAC GTC TTT AAG
Asn Tyr Cys Arg Asn Pro Asp Arg Asp Ser Lys Pro Trp Cys Tyr Val Phe Lys
                                 150
 600                 ·615                 630                 645
GCG GGG AAG TAC AGC TCA GAG TTC TGC AGC ACC CCT GCC TGC TCT GAG GGA AAC
Ala Gly Lys Tyr Ser Ser Glu Phe Cys Ser Thr Pro Ala Cys Ser Glu Gly Asn
 160                                      170
             660                 675                 690                 705
AGT GAC TGC TAC TTT GGG AAT GGG TCA GCC TAC CGT GGC ACG CAC AGC CTC ACC
Ser Asp Cys Tyr Phe Gly Asn Gly Ser Ala Tyr Arg Gly Thr His Ser Leu Thr
             180                                      190
```

FIG. 1B

```
              720                    735                    750
GAG TCG GGT GCC TCC TGC CTC CCG TGG AAT TCC ATG ATC CTG ATA GGC AAG GTT
Glu Ser Gly Ala Ser Cys Leu Pro Trp Asn Ser MET Ile Leu Ile Gly Lys Val
              200                                           210
      765                    780                    795                    810
TAC ACA GCA CAG AAC CCC AGT GCC CAG GCA CTG GGC CTG GGC AAA CAT AAT TAC
Tyr Thr Ala Gln Asn Pro Ser Ala Gln Ala Leu Gly Leu Gly Lys His Asn Tyr
                              220                                          230
              825                    840                    855
TGC CGG AAT CCT GAT GGG GAT GCC AAG CCC TGG TGC CAC GTG CTG AAG AAC CGC
Cys Arg Asn Pro Asp Gly Asp Ala Lys Pro Trp Cys His Val Leu Lys Asn Arg
                                     240
870                    885                    900                    915
AGG CTG ACG TGG GAG TAC TGT GAT GTG CCC TCC TGC TCC ACC TGC GGC CTG AGA
Arg Leu Thr Trp Glu Tyr Cys Asp Val Pro Ser Cys Ser Thr Cys Gly Leu Arg
250                                         260
              930                    945                    960            975
CAG TAC AGC CAG CCT CAG TTT CGC ATC AAA GGA GGG CTC TTC GCC GAC ATC GCC
Gln Tyr Ser Gln Pro Gln Phe Arg Ile Lys Gly Gly Leu Phe Ala Asp Ile Ala
              270                                           280
                     990                   1005                   1020
TCC CAC CCC TGG CAG GCT GCC ATC TTT GCC AAG CAC AGG AGG TCG CCC GGA GAG
Ser His Pro Trp Gln Ala Ala Ile Phe Ala Lys His Arg Arg Ser Pro Gly Glu
                     290                                          300
     1035                   1050                   1065                   1080
CGG TTC CTG TGC GGC GGC ATA CTC ATC AGC TCC TGC TGG ATT CTC TCT GCC GCC
Arg Phe Leu Cys Gly Gly Ile Leu Ile Ser Ser Cys Trp Ile Leu Ser Ala Ala
                            310                                          320
              1095                   1110                   1125
CAC TGC TTC CAG GAG AGG TTT CCG CCC CAC CAC CTG ACG GTG ATC TTG GGC AGA
His Cys Phe Gln Glu Arg Phe Pro Pro His His Leu Thr Val Ile Leu Gly Arg
                                     330
1140                   1155                   1170                   1185
ACA TAC CGG GTG GTC CCT GGC GAG GAG GAG CAG AAA TTT GAA GTC GAA AAA TAC
Thr Tyr Arg Val Val Pro Gly Glu Glu Glu Gln Lys Phe Glu Val Glu Lys Tyr
340                                         350
              1200                   1215                   1230            1245
ATT GTC CAT AAG GAA TTC GAT GAT GAC ACT TAC GAC AAT GAC ATT GCG CTG CTG
Ile Val His Lys Glu Phe Asp Asp Asp Thr Tyr Asp Asn Asp Ile Ala Leu Leu
              360                                           370
                     1260                   1275                   1290
CAG CTG AAA TCG GAT TCG TCC CGC TGT GCC CAG GAG AGC AGC GTG GTC CGC ACT
Gln Leu Lys Ser Asp Ser Ser Arg Cys Ala Gln Glu Ser Ser Val Val Arg Thr
                     380                                          390
     1305                   1320                   1335                   1350
GTG TGC CTT CCC CCG GCG GAC CTG CAG CTG CCG GAC TGG ACG GAG TGT GAG CTC
Val Cys Leu Pro Pro Ala Asp Leu Gln Leu Pro Asp Trp Thr Glu Cys Glu leu
                            400                                          410
              1365                   1380                   1395
TCC GGC TAC GGC AAG CAT GAG GCC TTG TCT CCT TTC TAT TCG GAG CGG CTG AAG
Ser Gly Tyr Gly Lys His Glu Ala Leu Ser Pro Phe Tyr Ser Glu Arg Leu Lys
                                     420
```

FIG. 1C

```
     1410                1425                1440                1455
GAG GCT CAT GTC AGA CTG TAC CCA TCC AGC CGC TGC ACA TCA CAA CAT TTA CTT
Glu Ala His Val Arg Leu Tyr Pro Ser Ser Arg Cys Thr Ser Gln His Leu Leu
430                                     440
          1470                1485                1500                1515
AAC AGA ACA GTC ACC GAC AAC ATG CTG TGT GCT GGA GAC ACT CGG AGC GGC GGG
Asn Arg Thr Val Thr Asp Asn MET Leu Cys Ala Gly Asp Thr Arg Ser Gly Gly
               450                                     460
               1530                1545                1560
CCC CAG GCA AAC TTG CAC GAC GCC TGC CAG GGC GAT TCG GGA GGC CCC CTG GTG
Pro Gln Ala Asn Leu His Asp Ala Cys Gln Gly Asp Ser Gly Gly Pro Leu Val
                    470                                     480
     1575                1590                1605                1620
TGT CTG AAC GAT GGC CGC ATG ACT TTG GTG GGC ATC ATC AGC TGG GGC CTG GGC
Cys Leu Asn Asp Gly Arg MET Thr Leu Val Gly Ile Ile Ser Trp Gly Leu Gly
                              490                                     500
               1635                1650                1665
TGT GGA CAG AAG GAT GTC CCG GGT GTG TAC ACA AAG GTT ACC AAC TAC CTA GAC
Cys Gly Gln Lys Asp Val Pro Gly Val Tyr Thr Lys Val Thr Asn Tyr Leu Asp
                                   510
1680                1695                1714       1724       1734
TGG ATT CGT GAC AAC ATG CGA CCG TGA CCAGGAACAC CCGACTCCTC AAAAGCAAAT GAGA
Trp Ile Arg Asp Asn MET Arg Pro
520                           527
```

FIGURE 1d

```
1290                    1305                    1320
 GTG GTC CGC ACT GTG TGC CTT CCC CCG GCG GAC CTG CAG CTG CCG
 Val Val Arg Thr Val Cys Leu Pro Pro Ala Asp Leu Gln Leu Pro
 390                                         400
1335                    1350                    1365
 GAC TGG ACG GAG TGT GAG CTC TCC GGC TAC GGC AAG CAT GAG GCC
 Asp Trp Thr Glu Cys Glu Leu Ser Gly Tyr Gly Lys His Glu Ala
                                 410
1380                    1395                    1410
 TTG TCT CCT TTC TAT TCG GAG CGG CTG AAG GAG GCT CAT GTC AGA
 Leu Ser Pro Phe Tyr Ser Glu Arg Leu Lys Glu Ala His Val Arg
 420                                         430
1425                    1440                    1455
 CTG TAC CCA TCC AGC CGC TGC ACA TCA CAA CAT TTA CTT AAC AGA
 Leu Tyr Pro Ser Ser Arg Cys Thr Ser Gln His Leu Leu Asn Arg
                                 440
1470                    1485                    1500
 ACA GTC ACC GAC AAC ATG CTG TGT GCT GGA GAC ACT CGG AGC GGC
 Thr Val Thr Asp Asn Met Leu Cys Ala Gly Asp Thr Arg Ser Gly
 450                                         460
1515                    1530                    1545
 GGG CCC CAG GCA AAC TTG CAC GAC GCC TGC CAG GGC GAT TCG GGA
 Gly Pro Gln Ala Asn Leu His Asp Ala Cys Gln Gly Asp Ser Gly
                                 470
1560                    1575                    1590
 GGC CCC CTG GTG TGT CTG AAC GAT GGC CGC ATG ACT TTG GTG GGC
 Gly Pro Leu Val Cys Leu Asn Asp Gly Arg Met Thr Leu Val Gly
 480                                         490
1605                    1620                    1635
 ATC ATC AGC TGG GGC CTG GGC TGT GGA CAG AAG GAT GTC CCG GGT
 Ile Ile Ser Trp Gly Leu Gly Cys Gly Gln Lys Asp Val Pro Gly
                                 500
1650                    1665                    1680
 GTG TAC ACA AAG GTT ACC AAC TAC CTA GAC TGG ATT CGT GAC AAC
 Val Tyr Thr Lys Val Thr Asn Tyr Leu Asp Trp Ile Arg Asp Asn
 510                                         520
1695                1714      1724      1734
 ATG CGA CCG TGA CCAGGAACAC CCGACTCCTC AAAAGCAAAT GAGATC
 Met Arg Pro
         527
```

```
            10         21         30         39         48
AAGCTTGGAT CCGCC ATG GAT GCA ATG AAG AGA GGG CTC TGC TGT GTG CTG CTG
                  MET Asp Ala MET Lys Arg Gly Leu Cys Cys Val Leu Leu 57         66         75         84         93        102
CTG TGT GGC GCC GTC TTC GTT TCG CCC AGC CAG GAA ATC CAT GCC CGA TTC AGA
Leu Cys Gly Ala Val Phe Val Ser Pro Ser Gln Glu Ile His Ala Arg Phe Arg 111        120        129        138        147        156
AGA GGA GCC AGA TCT TAC CAA GTG ATC TGC AGA GAT GAA AAA ACG CAG ATG ATA
Arg Gly Ala Arg Ser Tyr Gln Val Ile Cys Arg Asp Glu Lys Thr Gln MET Ile 165        174        183        192        201        210
TAC CAG CAA CAT CAG TCA TGG CTG CGC CCT GTG CTC AGA AGC AAC CGG GTG GAA
Tyr Gln Gln His Gln Ser Trp Leu Arg Pro Val Leu Arg Ser Asn Arg Val Glu 219        228        237        246        255        264
TAT TGC TGG TGC AAC AGT GGC AGG GCA CAG TGC CAC TCA GTG CCT GTC AAA AGT
Tyr Cys Trp Cys Asn Ser Gly Arg Ala Gln Cys His Ser Val Pro Val Lys Ser 273        282        291        300        309        318
TGC AGC GAG CCA AGG TGT TTC AAC GGG GGC ACC TGC CAG CAG GCC CTG TAC TTC
Cys Ser Glu Pro Arg Cys Phe Asn Gly Gly Thr Cys Gln Gln Ala Leu Tyr Phe 327        336        345        354        363        372
TCA GAT TTC GTG TGC CAG TGC CCC GAA GGA TTT GCT GGG AAG TGC TGT GAA ATA
Ser Asp Phe Val Cys Gln Cys Pro Glu Gly Phe Ala Gly Lys Cys Cys Glu Ile 381        390        399        408        417        426
GAT ACC AGG GCC ACG TGC TAC GAG GAC CAG GGC ATC AGC TAC AGG GGC ACG TGG
Asp Thr Arg Ala Thr Cys Tyr Glu Asp Gln Gly Ile Ser Tyr Arg Gly Thr Trp 435        444        453        462        471        480
AGC ACA GCG GAG AGT GGC GCC GAG TGC ACC AAC TGG AAC AGC AGC GCG TTG GCC
Ser Thr Ala Glu Ser Gly Ala Glu Cys Thr Asn Trp Asn Ser Ser Ala Leu Ala 489        498        507        516        525        534
CAG AAG CCC TAC AGC GGG CGG AGG CCA GAC GCC ATC AGG CTG GGC CTG GGG AAC
Gln Lys Pro Tyr Ser Gly Arg Arg Pro Asp Ala Ile Arg Leu Gly Leu Gly Asn 543        552        561        570        579        588
CAC AAC TAC TGC AGA AAC CCA GAT CGA GAC TCA AAG CCC TGG TGC TAC GTC TTT
His Asn Tyr Cys Arg Asn Pro Asp Arg Asp Ser Lys Pro Trp Cys Tyr Val Phe 597        606        615        624        633        642
AAG GCG GGG AAG TAC AGC TCA GAG TTC TGC AGC ACC CCT GCC TGC TCT GAG GGA
Lys Ala Gly Lys Tyr Ser Ser Glu Phe Cys Ser Thr Pro Ala Cys Ser Glu Gly 651        660        669        678        687        696
AAC AGT GAC TGC TAC TTT GGG AAT GGG TCA GCC TAC CGT GGC ACG CAC AGC CTC
Asn Ser Asp Cys Tyr Phe Gly Asn Gly Ser Ala Tyr Arg Gly Thr His Ser Leu 705        714        723        732        741        750
ACC GAG TCG GGT GCC TCC TGC CTC CCG TGG AAT TCC ATG ATC CTG ATA GGC AAG
Thr Glu Ser Gly Ala Ser Cys Leu Pro Trp Asn Ser MET Ile Leu Ile Gly Lys
```

FIG. 8A

```
759         768         777         786         795         804
GTT TAC ACA GCA CAG AAC CCC AGT GCC CAG GCA CTG GGC CTG GGC AAA CAT AAT
Val Tyr Thr Ala Gln Asn Pro Ser Ala Gln Ala Leu Gly Leu Gly Lys His Asn 813         822         831         840         849         858
TAC TGC CGG AAT CCT GAT GGG GAT GCC AAG CCC TGG TGC CAC GTG CTG AAG AAC
Tyr Cys Arg Asn Pro Asp Gly Asp Ala Lys Pro Trp Cys His Val Leu Lys Asn 867         876         885         894         903         912
CGC AGG CTG ACG TGG GAG TAC TGT GAT GTG CCC TCC TGC GCG GTA CCT TCA TTT
Arg Arg Leu Thr Trp Glu Tyr Cys Asp Val Pro Ser Cys Ala Val Pro Ser Phe 921         930         939         948         957         966
GAT TGT GGG AAG CCT CAA GTG GAG CCG AAG AAA TGT CCT GGA AGG GTT GTA GGG
Asp Cys Gly Lys Pro Gln Val Glu Pro Lys Lys Cys Pro Gly Arg Val Val Gly 975         984         993         1002        1011        1020
GGG TGT GTG GCC CAC CCA CAT TCC TGG CCC TGG CAA GTC AGT CTT AGA ACA AGG
Gly Cys Val Ala His Pro His Ser Trp Pro Trp Gln Val Ser Leu Arg Thr Arg 1029        1038        1047        1056        1065        1074
TTT GGA ATG CAC TTC TGT GGA GGC ACC TTG ATA TCC CCA GAG TGG GTG TTG ACT
Phe Gly MET His Phe Cys Gly Gly Thr Leu Ile Ser Pro Glu Trp Val Leu Thr 1083        1092        1101        1110        1119        1128
GCT GCC CAC TGC TTG GAG AAG TCC CCA AGG CCT TCA TCC TAC AAG GTC ATC CTG
Ala Ala His Cys Leu Glu Lys Ser Pro Arg Pro Ser Ser Tyr Lys Val Ile Leu 1137        1146        1155        1164        1173        1182
GGT GCA CAC CAA GAA GTG AAT CTC GAA CCG CAT GTT CAG GAA ATA GAA GTG TCT
Gly Ala His Gln Glu Val Asn Leu Glu Pro His Val Gln Glu Ile Glu Val Ser 1191        1200        1209        1218        1227        1236
AGG CTG TTC TTG GAG CCC ACA CGA AAA GAT ATT GCC TTG CTA AAG CTA AGC AGT
Arg Leu Phe Leu Glu Pro Thr Arg Lys Asp Ile Ala Leu Leu Lys Leu Ser Ser 1245        1254        1263        1272        1281        1290
CCT GCC GTC ATC ACT GAC AAA GTA ATC CCA GCT TGT CTG CCA TCC CCA AAT TAT
Pro Ala Val Ile Thr Asp Lys Val Ile Pro Ala Cys Leu Pro Ser Pro Asn Tyr 1299        1308        1317        1326        1335        1344
GTG GTC GCT GAC CGG ACC GAA TGT TTC ATC ACT GGC TGG GGA GAA ACC CAA GGT
Val Val Ala Asp Arg Thr Glu Cys Phe Ile Thr Gly Trp Gly Glu Thr Gln Gly 1353        1362        1371        1380        1389        1398
ACT TTT GGA GCT GGC CTT CTC AAG GAA GCC CAG CTC CCT GTG ATT GAG AAT AAA
Thr Phe Gly Ala Gly Leu Leu Lys Glu Ala Gln Leu Pro Val Ile Glu Asn Lys 1407        1416        1425        1434        1443        1452
GTG TGC AAT CGC TAT GAG TTT CTG AAT GGA AGA GTC CAA TCC ACC GAA CTC TGT
Val Cys Asn Arg Tyr Glu Phe Leu Asn Gly Arg Val Gln Ser Thr Glu Leu Cys 1461        1470        1479        1488        1497        1506
GCT GGG CAT TTG GCC GGA GGC ACT GAC AGT TGC CAG GGT GAC AGT GGA GGT CCT
Ala Gly His Leu Ala Gly Gly Thr Asp Ser Cys Gln Gly Asp Ser Gly Gly Pro
```

*FIG. 8B*

```
1515          1524          1533          1542          1551          1560
CTG GTT TGC TTC GAG AAG GAC AAA TAC ATT TTA CAA GGA GTC ACT TCT TGG GGT
Leu Val Cys Phe Glu Lys Asp Lys Tyr Ile Leu Gln Gly Val Thr Ser Trp Gly 1569          1578          1587          1596          1605          1614
CTT GGC TGT GCA CGC CCC AAT AAG CCT GGT GTC TAT GTT CGT GTT TCA AGG TTT
Leu Gly Cys Ala Arg Pro Asn Lys Pro Gly Val Tyr Val Arg Val Ser Arg Phe 1623          1632          1641          1650                  1666          1676
GTT ACT TGG ATT GAG GGA GTG ATG AGA AAT AAT TAA TTGGACGGGA GACAGAGTGA
Val Thr Trp Ile Glu Gly Val MET Arg Asn Asn   .

1686          1696          1706          1716
CGCACTGACT CACCTAGAGG CTGGAACGAG GGTAGGGATT TAGCATGC
```

*FIG. 8C*

```
                  10              20              30              39              48              57
          GCACTGCTGG CCAGTCCCAA A ATG GAA CAT AAG GAA GTG GTT CTT CTA CTT CTT TTA
                                  Met Glu His Lys Glu Val Val Leu Leu Leu Leu Leu 66              75              84              93              102             111
          TTT CTG AAA TCA GGT CAA GGA GAG CCT CTG GAT GAC TAT GTG AAT ACC CAG GGG
          Phe Leu Lys Ser Gly Gln Gly Glu Pro Leu Asp Asp Tyr Val Asn Thr Gln Gly 120             129             138             147             156             165
          GCT TCA CTG TTC AGT GTC ACT AAG AAG CAG CTG GGA GCA GGA AGT ATA GAA GAA
          Ala Ser Leu Phe Ser Val Thr Lys Lys Gln Leu Gly Ala Gly Ser Ile Glu Glu 174             183             192             201             210             219
          TGT GCA GCA AAA TGT GAG GAG GAC GAA GAA TTC ACC TGC AGG GCA TTC CAA TAT
          Cys Ala Ala Lys Cys Glu Glu Asp Glu Glu Phe Thr Cys Arg Ala Phe Gln Tyr 228             237             246             255             264             273
          CAC AGT AAA GAG CAA CAA TGT GTG ATA ATG GCT GAA AAC AGG AAG TCC TCC ATA
          His Ser Lys Glu Gln Gln Cys Val Ile Met Ala Glu Asn Arg Lys Ser Ser Ile 282             291             300             309             318             327
          ATC ATT AGG ATG AGA GAT GTA GTT TTA TTT GAA AAG AAA GTG TAT CTC TCA GAG
          Ile Ile Arg Met Arg Asp Val Val Leu Phe Glu Lys Lys Val Tyr Leu Ser Glu 336             345             354             363             372             381
          TGC AAG ACT GGG AAT GGA AAG AAC TAC AGA GGG ACG ATG TCC AAA ACA AAA AAT
          Cys Lys Thr Gly Asn Gly Lys Asn Tyr Arg Gly Thr Met Ser Lys Thr Lys Asn 390             399             408             417             426             435
          GGC ATC ACC TGT CAA AAA TGG AGT TCC ACT TCT CCC CAC AGA CCT AGA TTC TCA
          Gly Ile Thr Cys Gln Lys Trp Ser Ser Thr Ser Pro His Arg Pro Arg Phe Ser 444             453             462             471             480             489
          CCT GCT ACA CAC CCC TCA GAG GGA CTG GAG GAG AAC TAC TGC AGA AAT CCA GAC
          Pro Ala Thr His Pro Ser Glu Gly Leu Glu Glu Asn Tyr Cys Arg Asn Pro Asp 498             507             516             525             534             543
          AAC GAT CCG CAG GGG CCC TGG TGC TAT ACT ACT GAT CCA GAA AAG AGA TAT GAC
          Asn Asp Pro Gln Gly Pro Trp Cys Tyr Thr Thr Asp Pro Glu Lys Arg Tyr Asp 552             561             570             579             588             597
          TAC TGC GAC ATT CTT GAG TGT GAA GAG GAA TGT ATG CAT TGC AGT GGA GAA AAC
          Tyr Cys Asp Ile Leu Glu Cys Glu Glu Glu Cys Met His Cys Ser Gly Glu Asn 606             615             624             633             642             651
          TAT GAC GGC AAA ATT TCC AAG ACC ATG TCT GGA CTG GAA TGC CAG GCC TGG GAC
          Tyr Asp Gly Lys Ile Ser Lys Thr Met Ser Gly Leu Glu Cys Gln Ala Trp Asp 660             669             678             687             696             705
          TCT CAG AGC CCA CAC GCT CAT GGA TAC ATT CCT TCC AAA TTT CCA AAC AAG AAC
          Ser Gln Ser Pro His Ala His Gly Tyr Ile Pro Ser Lys Phe Pro Asn Lys Asn 714             723             732             741             750             759
          CTG AAG AAG AAT TAC TGT CGT AAC CCC GAG AGG GAG CTG CGG CCT TGG TGT TTC
          Leu Lys Lys Asn Tyr Cys Arg Asn Pro Glu Arg Glu Leu Arg Pro Trp Cys Phe
```

*FIG. 10A*

```
         768         777         786          795         804         813
ACC ACC GAC CCC AAC AAG CGC TGG GAA CTT TGT GAC ATC CCC CGC TGC ACA ACA
Thr Thr Asp Pro Asn Lys Arg Trp Glu Leu Cys Asp Ile Pro Arg Cys Thr Thr 822         831         840          849         858         867
CCT CCA CCA TCT TCT GGT CCC ACC TAC CAG TGT CTG AAG GGA ACA GGT GAA AAC
Pro Pro Pro Ser Ser Gly Pro Thr Tyr Gln Cys Leu Lys Gly Thr Gly Glu Asn 876         885         894          903         912         921
TAT CGC GGG AAT GTG GCT GTT ACC GTG TCC GGG CAC ACC TGT CAG CAC TGG AGT
Tyr Arg Gly Asn Val Ala Val Thr Val Ser Gly His Thr Cys Gln His Trp Ser 930         939         948          957         966         975
GCA CAG ACC CCT CAC ACA CAT AAC AGG ACA CCA GAA AAC TTC CCC TGC AAA AAT
Ala Gln Thr Pro His Thr His Asn Arg Thr Pro Glu Asn Phe Pro Cys Lys Asn 984         993        1002         1011        1020        1029
TTG GAT GAA AAC TAC TGC CGC AAT CCT GAC GGA AAA AGG GCC CCA TGG TGC CAT
Leu Asp Glu Asn Tyr Cys Arg Asn Pro Asp Gly Lys Arg Ala Pro Trp Cys His 1038        1047        1056         1065        1074        1083
ACA ACC AAC AGC CAA GTG CGG TGG GAG TAC TGT AAG ATA CCG TCC TGT GAC TCC
Thr Thr Asn Ser Gln Val Arg Trp Glu Tyr Cys Lys Ile Pro Ser Cys Asp Ser 1092        1101        1110         1119        1128        1137
TCC CCA GTA TCC ACG GAA CAA TTG GCT CCC ACA GCA CCA CCT GAG CTA ACC CCT
Ser Pro Val Ser Thr Glu Gln Leu Ala Pro Thr Ala Pro Pro Glu Leu Thr Pro 1146        1155        1164         1173        1182        1191
GTG GTC CAG GAC TGC TAC CAT GGT GAT GGA CAG AGC TAC CGA GGC ACA TCC TCC
Val Val Gln Asp Cys Tyr His Gly Asp Gly Gln Ser Tyr Arg Gly Thr Ser Ser 1200        1209        1218         1227        1236        1245
ACC ACC ACC ACA GGA AAG AAG TGT CAG TCT TGG TCA TCT ATG ACA CCA CAC CGG
Thr Thr Thr Thr Gly Lys Lys Cys Gln Ser Trp Ser Ser Met Thr Pro His Arg 1254        1263        1272         1281        1290        1299
CAC CAG AAG ACC CCA GAA AAC TAC CCA AAT GCT GGC CTG ACA ATG AAC TAC TGC
His Gln Lys Thr Pro Glu Asn Tyr Pro Asn Ala Gly Leu Thr Met Asn Tyr Cys 1308        1317        1326         1335        1344        1353
AGG AAT CCA GAT GCC GAT AAA GGC CCC TGG TGT TTT ACC ACA GAC CCC AGC GTC
Arg Asn Pro Asp Ala Asp Lys Gly Pro Trp Cys Phe Thr Thr Asp Pro Ser Val 1362        1371        1380         1389        1398        1407
AGG TGG GAG TAC TGC AAC CTG AAA AAA TGC TCA GGA ACA GAA GCG AGT GTT GTA
Arg Trp Glu Tyr Cys Asn Leu Lys Lys Cys Ser Gly Thr Glu Ala Ser Val Val 1416        1425        1434         1443        1452        1461
GCA CCT CCG CCT GTT GTC CTG CTT CCA GAT GTA GAG ACT CCT TCC GAA GAA GAC
Ala Pro Pro Pro Val Val Leu Leu Pro Asp Val Glu Thr Pro Ser Glu Glu Asp 1470        1479        1488         1497        1506        1515
TGT ATG TTT GGG AAT GGG AAA GGA TAC CGA GGC AAG AGG GCG ACC ACT GTT ACT
Cys Met Phe Gly Asn Gly Lys Gly Tyr Arg Gly Lys Arg Ala Thr Thr Val Thr
```

*FIG. 10B*

```
     1524         1533         1542         1551         1560         1569
GGG ACG CCA TGC CAG GAC TGG GCT GCC CAG GAG CCC CAT AGA CAC AGC ATT TTC
Gly Thr Pro Cys Gln Asp Trp Ala Ala Gln Glu Pro His Arg His Ser Ile Phe 1578         1587         1596         1605         1614         1623
ACT CCA GAG ACA AAT CCA CGG GCG GGT CTG GAA AAA AAT TAC TGC CGT AAC CCT
Thr Pro Glu Thr Asn Pro Arg Ala Gly Leu Glu Lys Asn Tyr Cys Arg Asn Pro 1632         1641         1650         1659         1668         1677
GAT GGT GAT GTA GGT GGT CCC TGG TGC TAC ACG ACA AAT CCA AGA AAA CTT TAC
Asp Gly Asp Val Gly Gly Pro Trp Cys Tyr Thr Thr Asn Pro Arg Lys Leu Tyr 1686         1695         1704         1713         1722         1731
GAC TAC TGT GAT GTC CCT CAG TGT GCG GCC CCT TCA TTT GAT TGT GGG AAG CCT
Asp Tyr Cys Asp Val Pro Gln Cys Ala Ala Pro Ser Phe Asp Cys Gly Lys Pro 1740         1749         1758         1767         1776         1785
CAA GTG GAG CCG AAG AAA TGT CCT GGA AGG GTT GTA GGG GGG TGT GTG GCC CAC
Gln Val Glu Pro Lys Lys Cys Pro Gly Arg Val Val Gly Gly Cys Val Ala His 1794         1803         1812         1821         1830         1839
CCA CAT TCC TGG CCC TGG CAA GTC AGT CTT AGA ACA AGG TTT GGA ATG CAC TTC
Pro His Ser Trp Pro Trp Gln Val Ser Leu Arg Thr Arg Phe Gly Met His Phe 1848         1857         1866         1875         1884         1893
TGT GGA GGC ACC TTG ATA TCC CCA GAG TGG GTG TTG ACT GCT GCC CAC TGC TTG
Cys Gly Gly Thr Leu Ile Ser Pro Glu Trp Val Leu Thr Ala Ala His Cys Leu 1902         1911         1920         1929         1938         1947
GAG AAG TCC CCA AGG CCT TCA TCC TAC AAG GTC ATC CTG GGT GCA CAC CAA GAA
Glu Lys Ser Pro Arg Pro Ser Ser Tyr Lys Val Ile Leu Gly Ala His Gln Glu 1956         1965         1974         1983         1992         2001
GTG AAT CTC GAA CCG CAT GTT CAG GAA ATA GAA GTG TCT AGG CTG TTC TTG GAG
Val Asn Leu Glu Pro His Val Gln Glu Ile Glu Val Ser Arg Leu Phe Leu Glu 2010         2019         2028         2037         2046         2055
CCC ACA CGA AAA GAT ATT GCC TTG CTA AAG CTA AGC AGT CCT GCC GTC ATC ACT
Pro Thr Arg Lys Asp Ile Ala Leu Leu Lys Leu Ser Ser Pro Ala Val Ile Thr 2064         2073         2082         2091         2100         2109
GAC AAA GTA ATC CCA GCT TGT CTG CCA TCC CCA AAT TAT GTG GTC GCT GAC CGG
Asp Lys Val Ile Pro Ala Cys Leu Pro Ser Pro Asn Tyr Val Val Ala Asp Arg 2118         2127         2136         2145         2154         2163
ACC GAA TGT TTC ATC ACT GGC TGG GGA GAA ACC CAA GGT ACT TTT GGA GCT GGC
Thr Glu Cys Phe Ile Thr Gly Trp Gly Glu Thr Gln Gly Thr Phe Gly Ala Gly 2172         2181         2190         2199         2208         2217
CTT CTC AAG GAA GCC CAG CTC CCT GTG ATT GAG AAT AAA GTG TGC AAT CGC TAT
Leu Leu Lys Glu Ala Gln Leu Pro Val Ile Glu Asn Lys Val Cys Asn Arg Tyr 2226         2235         2244         2253         2262         2271
GAG TTT CTG AAT GGA AGA GTC CAA TCC ACC GAA CTC TGT GCT GGG CAT TTG GCC
Glu Phe Leu Asn Gly Arg Val Gln Ser Thr Glu Leu Cys Ala Gly His Leu Ala
```

*FIG. 10C*

```
              2280        2289         2298         2307         2316         2325
         GGA GGC ACT GAC AGT TGC CAG GGT GAC AGT GGA GGT CCT CTG GTT TGC TTC GAG
         Gly Gly Thr Asp Ser Cys Gln Gly Asp Ser Gly Gly Pro Leu Val Cys Phe Glu 2334        2343         2352         2361         2370         2379
         AAG GAC AAA TAC ATT TTA CAA GGA GTC ACT TCT TGG GGT CTT GGC TGT GCA CGC
         Lys Asp Lys Tyr Ile Leu Gln Gly Val Thr Ser Trp Gly Leu Gly Cys Ala Arg 2388        2397         2406         2415         2424         2433
         CCC AAT AAG CCT GGT GTC TAT GTT CGT GTT TCA AGG TTT GTT ACT TGG ATT GAG
         Pro Asn Lys Pro Gly Val Tyr Val Arg Val Ser Arg Phe Val Thr Trp Ile Glu 2442        2451         2464         2474         2484         2494
         GGA GTG ATG AGA AAT AAT TAA TTGGACGGGA GACAGAGTGA CGCACTGACT CACCTAGAGG
         Gly Val Met Arg Asn Asn  .

2504         2514         2524         2534         2544         2554         2564
         CTGGAACGAG GGTAGGGATT TAGCATGCTG GAAATAACTG GCAGTAATCA AACGAAGACA CTGTCCCCAG 2574         2584         2594         2604         2614         2624         2634
         CTACCAGCTA CGCCAAACCT CGGCATTTTT TGTGTTATTT TCTGACTGCT GGATTCTGTA GTAAGGTGAC 2644         2654         2664         2674
         ATAGCTATGA CATTTGTTAA AAATAAACTC TGTACTTAAC TTTGA
```

*FIG. 10D*

Activation of pMH 10 by Thrombin

THROMBIN-ACTIVATED TISSUE PLASMINOGEN ACTIVATORS

TECHNICAL FIELD

The present invention relates to fibrinolytic agents in general, and more specifically, to fibrinolytic agents which are activated upon cleavage by thrombin.

BACKGROUND ART

Blood coagulation is a process consisting of a complex interaction of various blood components which eventually gives rise to a fibrin network, or clot. Degradation of the fibrin network can be accomplished by activation of the zymogen plasminogen into plasmin, a serine protease which acts directly to degrade the fibrin network and thereby regulate the coagulation process. Conversion of plasminogen into plasmin is normally catalyzed in vivo by tissue-type plasminogen activator (t-PA), a fibrin-specific serine protease which is believed to be the physiological vascular activator of plasminogen. Urokinase-type plasminogen activator (u-PA) is another member of the class of plasminogen activators characterized as serine proteases. t-PA and u-PA are functionally and immunologically distinguishable.

t-PA normally circulates as a single polypeptide chain of $M_r \approx 72,000$ daltons which is converted to a two-chain form by cleavage of a peptide bond between amino acids 275 (Arg) and 276 (Ile). This cleavage is catayzed by trypsin or plasmin, and is accompanied by an increase in activity as measured using synthetic substrates, and by an increase in fibrinolytic activity. Fibrinolytic activity of t-PA is enhanced upon binding to fibrin, due in part to the high concentrations of plasminogen and t-PA present on the surface of a fibrin clot. Cleavage to the two-chain form may also be associated with rapid clearance of t-PA from the bloodstream, but conflicting reports on this have been published (see Wallen et al., *Eur. J. Biochem.* 132: 681–686, 1983).

A two-dimensional model of the potential precursor t-PA protein has been established (Ny et al., *Proc. Natl. Acad. Sci. USA* 81: 5355–5359, 1984). From this model, it was determined that the heavy chain contains two triple disulfide structures known as "kringles." These kringle structures also occur in prothrombin, plasminogen and urokinase, and are believed to be important for binding to fibrin (Ny et al., ibid.). The second kringle (K$_2$) of t-PA is believed to have a higher affinity for fibrin than the first kringle (K$_1$) (Ichinose, Takio and Fujikawa, *J. Clin. Invest.* 78: 163–169, 1986). The heavy chain of t-PA (two variants of $M_r$ 40,000 and 37,000) is derived from the amino-terminus, while the light chain ($M_r$ 33,000) is derived from the carboxy-terminal end of the t-PA molecule.

The heavy chain of t-PA also contains a "finger" domain that is homologous to the finger domains of fibronectin. Fibronectin has been implicated in a variety of biological activities, including fibrin binding, and the fibrin binding activity has been correlated to four or five of the nine finger domains possessed by fibronectin. The heavy chain of t-PA also contains a growth factor-like domain.

The light chain of t-PA contains the active site for serine protease activity, which is highly homologous to the active sites of other serine proteases.

Native t-PA additionally comprises a pre-region followed downstream by a pro-region, which are collectively referred to as the "pre-pro" region. The pre-region contains a signal peptide which is important for secretion of t-PA by vascular endothelial cells (Ny et al., ibid.). The pre sequence is believed responsible for secretion of t-PA into the lumen of the endoplasmic reticulum, a necessary step in extracellular secretion. The pro sequence is believed to be cleaved from the t-PA molecule following transport from the endoplasmic reticulum to the Golgi apparatus.

Urokinase exhibits structural features similar to those of t-PA. The precursor form of the molecule has the structure pre-pro-growth factor-kringle-serine protease. The zymogen pro-urokinase is activated upon cleavage at an activation site between the kringle and serine protease domains by plasmin, trypsin, or plasma kallikrein (Ichinose et al., *J. Biol. Chem.* 261: 3486–3489, 1986). Urokinase also contains a thrombin cleavage site adjacent to the activation site. Cleavage by thrombin results in inactivation of the protein (Ichinose et al., ibid.).

The structure and activation of plasminogen are reviewed by Collen (*Thromb. Haemostasis* 43: 77–89, 1980). Briefly, plasminogen is a single-chain glycoprotein of $M_r \approx 90,000$ (designated "Glu-plasminogen") comprising five kringle structures and a carboxyl-terminal serine protease domain. Activation of plasminogen to plasmin is a multistep process involving the removal of an aminoterminal peptide (conversion to Lys-plasminogen) and cleavage at the activation site to produce the active, two-chain protein. Glu-plasminogen may also be cleaved at the activation site, followed by removal of the amino-terminal peptide.

Urokinase has a low affinity for fibrin and activates plasminogen throughout the body. While t-PA is more specific for cleavage of plasminogen in the presence of fibrin (i.e., at the site of a clot), therapeutic doses of t-PA sufficient to lyse coronary thrombi are far larger than normal physiological levels. Further, doses of this size may also activate plasminogen throughout the body, leading to systemic degradation of fibrinogen (Sherry, *New Eng. J. Med.* 313: 1014–1017, 1985), which results in dangerous bleeding episodes. The systemic activity of t-PA may be due to activation by a low level of free plasmin in the circulation or to proteolytic activity of the two-chain form of t-PA used in the clinical studies.

These side effects of t-PA have been recognized, and several approaches have been employed in an attempt to create an improved form of t-PA. For example, Heyneker and Vehar (GB 2,173,804) disclose modified t-PA molecules alleged to have increased specificity. In addition, Rosa and Rosa (International Patent Application WO 86/01538) modified the sequence around the activation site of t-PA with the aim of increasing the half-life.

Although these attempts have met with some degree of success, within clinical applications, it would be advantageous to employ fibrinolytic agents possessing a higher specificity for catalytic activity at the clot site than is observed for the naturally-occurring plasminogen activators. The present invention fulfills the need for a fibrinolytic agent which combines the clinical efficacy of t-PA with minimal undesirable side effects by providing novel, highly specific fibrinolytic agents which may be produced in relatively large quantities. Through the use of recombinant DNA technology, a consistent and homogeneous source of these fibrinolytic agents is provided. These fibrinolytic agents can be utilized to lyse existing clots in heart attack and stroke victims, and in other patients where the need to lyse clots or suppress the formation of fibrin matrices is therapeutically desirable.

DISCLOSURE OF THE INVENTION

Briefly stated, the present invention discloses zymogens of proteins having fibrinolytic activity. The proteins are cleavable by thrombin, the cleavage resulting in stimulation of fibrinolytic activity. The methods described herein may be utilized to modify the zymogens of a variety of proteins, such as tissue plasminogen activator, urokinase, plasminogen variants, such as mini-plasminogen (Val (442) plasminogen; Sottrup-Jensen et al., in: *Progress in Chemical Fibrinolysis anc Thrombolysis*, Raven Press, New York, 1978, vol. 3, pp. 191–209), Lys-plasminogen and Glu-plasminogen, such that they are activated upon cleavage by thrombin. This activation occurs through specific cleavage of the precursor fibrinolytic molecule at or near the normal activation site. Modifications such as those described herein result in a molecule that is relatively clot-specific, in view of the probability that large amounts of thrombin would be associated with clots in vivo.

In addition, modifications such as those described herein, which result in a molecule which is activated upon cleavage by thrombin rather than plasmin, should result in the reduction or elimination of the proteolytic effects of plasmin which are normally associated with the production and secretion of t-PA by recombinant mammalian cells in serum-containing media. These modifications should have a similar effect upon the production of urokinase in recombinant cells.

In one aspect of the present invention, the zymogen contains an amino acid substitution at the P2 position. Preferred substituted amino acids include leucine, isoleucine, valine, and proline, the latter being particularly preferred.

In addition to an amino acid substitution at position P2, the zymogen may contain an amino acid substitution at one or more of the positions P6 through P13, the substitutions selected to afford a resulting increase in the acidic character of the zymogen. Preferred amino acid substitutions in this regard include aspartic acid and glutamic acid. Similarly, the zymogen may contain an aromatic amino acid residue, such as Trp, Tyr, or Phe, preferably phenylalanine at position P3, P9, P11, P12 and/or P13, in addition to an amino acid substitution at position P2. The present invention includes any combination of the described amino acid substitutions.

In addition to naturally-occurring plasminogen activators, variant forms of t-PA and u-PA may be further modified according to the present invention to include a thrombin activation site. Plasminogen activators which are hybrid molecules comprising portions of the various activators and/or plasminogen may also be modified. By way of example, suitable fibrinolytically active hybrid proteins are disclosed in EP 155,387. Briefly, these hybrids are characterized as comprising two chains derived from different two-chain proteases, such as plasmin A-chain and t-PA B-chain. Furthermore, as noted above, plasminogen itself or variants of plasminogen may be modified to include a thrombin-cleavable activation site. This modification results in a fibrinolytic enzyme which is directly activated by thrombin present at the clot site, without the need for an intermediate plasminogen activator. This is expected to be advantageous in comparison with existing fibrinolytic agents which are activated by other fibrinolytic, rather than coagulant, enzymes.

Within a related aspect of the present invention, pharmaceutical compositions are disclosed comprising a zymogen of a protein having fibrinolytic activity that is cleavable by thrombin, the cleavage resulting in stimulation of the fibrinolytic activity, and a physiologically acceptable carrier and/or diluent. These zymogens may contain amino acid substitutions similar to those described above. Suitable carriers or diluents include sterile water and sterile saline. Administration is by injection or infusion.

These and other aspects of the present invention will become evident upon reference to the following detailed description and attached drawings.

BRIEF DESCRIPTION OF THE DRAWINGS

FIG. 1 parts A, B, C and D illustrates the pre-pro t-PA coding sequence constructed from cDNA and synthesized oligonucleotides, together with the amino acid sequence of the encoded protein. Numbers above the lines refer to nucleotide position and numbers below the lines refer to amino acid position.

FIG. 5 illustrates the construction of plasmid p820a.

FIG. 8 parts A, B and C illustrates the DNA sequence encoding a t-PA/plasminogen hybrid protein and the amino acid sequence of the protein.

FIG. 10 parts A, B, C and D shows the sequence of a plasminogen cDNA.

BEST MODE FOR CARRYING OUT THE INVENTION

Figure 2:
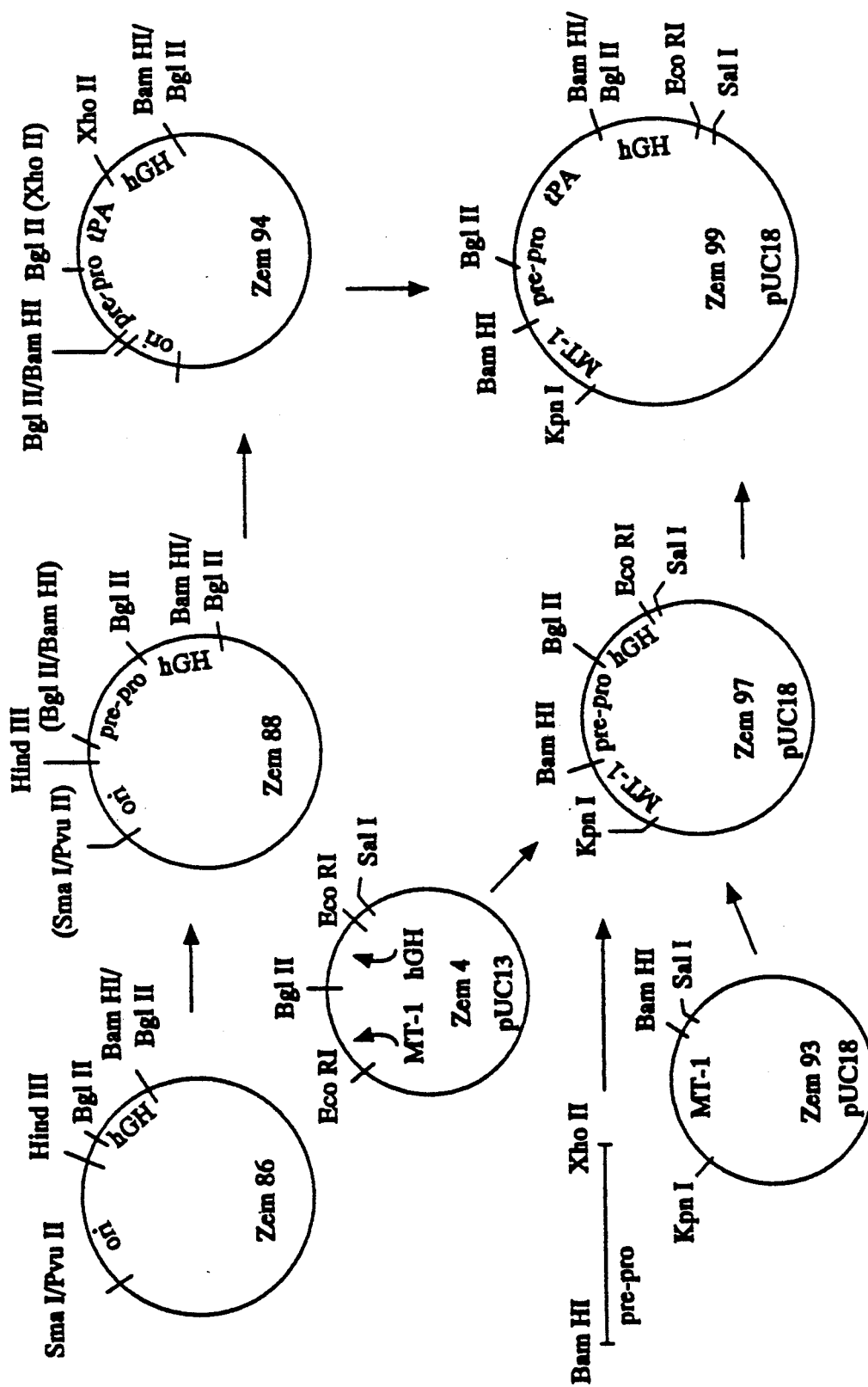
FIG. 2 illustrates the construction of the vector Zem99.

Prior to setting forth the invention, it may be helpful to an understanding thereof to set forth definitions of certain terms used herein.

Complementary DNA or cDNA: A DNA molecule or sequence which has been enzymatically synthesized from the sequences present in an mRNA template.

DNA construct: A DNA molecule, or a clone of such a molecule, either single- or double-stranded, which has been modified through human intervention to contain segments of DNA combined and juxtaposed in a manner which would not otherwise exist in nature.

Plasmid or vector: A DNA construct containing genetic information which provides for its replication when inserted into a host cell. Replication may be autonomous or achieved by integration into the host genome. A plasmid generally contains at least one gene sequence to be expressed in the host cell, as well as sequences encoding functions which facilitate such gene expression, including promoters, transcription initiation sites and transcription terminators. It may be a linear molecule or a closed, circular molecule.

Pre-pro region: An amino acid sequence which generally occurs at the amino-termini of the precursors of certain proteins, and which is generally cleaved from the protein, at least in part, during secretion. The pre-pro region comprises, in part, sequences directing the protein into the secretory pathway of the cell and generally contains a region rich in hydrophobic amino acids.

Domain: A three-dimensional, self-assembling array of amino acids of a protein molecule, which contains structural elements necessary for a specific biological activity of that protein.

Fibrin-binding domain: That portion of a protein necessary for the binding of that protein to fibrin. In native t-PA, the finger domain and kringle structures individually and collectively contribute to the fibrin binding. As disclosed herein and in co-pending, U.S. patent application Ser. No. 822,005, it has been found that the growth factor domain is not required for fibrin binding of t-PA or modified t-PAs.

Biological activity: The function or set of functions performed by a molecule in a biological context (i.e., in an organism, a cell, or an in vitro facsimile thereof). Biological activities of proteins may be divided into catalytic and effector activities. Catalytic activities of fibrinolytic agents often involve the activation of other proteins through specific cleavage of precursors. In contrast, effector activities include specific binding of the biologically active molecule to other molecules, such as fibrin, or to cells. Effector activity frequently augments, or is essential to, catalytic activity under physiological conditions. Catalytic and effector activities may, in some cases, reside in the same domain of the protein. For plasminogen activators, biological activity is characterized by the conversion of the pro-enzyme or zymogen plasminogen into plasmin, which in turn degrades fibrin matrices. Because fibrin acts as a cofactor in the activation of plasminogen by t-PA, native t-PA has relatively little activity in the absence of fibrin. As used herein, the phrase "fibrinolytic activity" is given a functional definition based on observed in vivo or in vitro effects. Fibrinolytic activity is the stimulation of fibrinolysis, either directly, as in the case of plasmin, which acts directly on fibrin, or indirectly, as in the case of the plasminogen activators, which stimulate fibrinolysis through their action on another fibrinolytic agent, plasminogen.

Fibrinolytic agent: A polypeptide having fibrinolytic activity or a precursor or zymogen of such a protein. Precursors may have some basal level of activity.

Activation site: A bond between adjacent amino acids in a protein, the cleavage of which results in the enhancement of the biological activity of the protein. Amino acid residues in a protein may be numbered according to their positions relative to an activation site. Those amino acids upstream (N-terminal) of the activation site are numbered P1, P2, P3, etc., the number increasing with distance from the activation site. Those downstream of the activation site are numbered P1', P2', P3', etc.

As noted above, the present invention discloses the modification of a variety of naturally occurring plasminogen activators, as well as variant forms thereof, to include a thrombin activation site. Many examples of variant plasminogen activators have been reported which are suitable for modification and subsequent use within the present invention. These include unglycosylated forms of urokinase and t-PA (WO 84/01786), truncated forms of t-PA (van Zonneveld et al., *Proc. Natl. Acad. Sci. USA* 83: 4670–4674, 1986, and co-pending, U.S. patent application Ser. No. 822,005, herein incorporated by reference), and hybrid molecules comprising light and heavy chains derived from different fibrinolytic proteins (EP 155,387). Additional modified forms of t-PA have been described by Rosa and Rosa (ibid.), who modified the Lys at position 277 of t-PA to stabilize the single-chain form of the protein, and Heyneker and Vehar (GB 2,173,804), who disclosed amino acid substitutions around the cleavage site of t-PA. Additional suitable fibrinolytic agents may comprise amino acid deletions, amino acid substitutions, or combinations of amino acid deletions and substitutions at or near the activation (cleavage) site. All of these variant fibrinolytic molecules may be further modified as described herein to include a thrombin-cleavable activation site.

As indicated above, the fibrinolytic agents t-PA, u-PA, and plasminogen are converted to their active forms by enzymatic cleavage by trypsin or plasmin (in the case of t-PA), by a plasminogen activator (in the case of plasminogen), or by trypsin, plasma kallikrein or plasmin (in the case of u-PA). However, because the plasminogen activators exhibit nonspecific activity, it is desirable to provide novel fibrinolytic agents which act only at the site of a clot. These clot-specific fibrinolytic agents are derived from the plasminogen activators or from plasminogen itself.

An analysis of the cleavage sites for many of the blood serine proteases has indicated that much of the specificity of cleavage for these proteases may reside in the amino acid sequence surrounding the substrate target site(s). In the case of t-PA, this target site is amino acids 275-276. One of the thrombin-cleavable fibrinolytic agents disclosed herein is a mutant form of t-PA in which the phenylalanine at position 274 has been replaced by proline. This protein, as well as native recombinant t-PA, was incubated with catalytic amounts of bovine thrombin. Aliquots of the reaction mixture were removed at different time intervals and assayed for t-PA amidolytic activity with the substrate S-2444. The modified t-PA (designated "pMH10") was found to be rapidly converted to an active form by incubation with thrombin, whereas no conversion of native t-PA was seen.

To demonstrate that thrombin was cleaving the modified t-PA to cause this activation, the activation reaction was repeated, and aliquots of each time point were analyzed on a Western blot. The results clearly showed the appearance of a two-chain form of the modified t-PA in the test samples, coincident with the appearance of amidolytic activity. No two-chain form was seen in the control sample without thrombin or in the native t-PA control with or without thrombin. Thus there appears to be a specific cleavage of this mutant protein by thrombin at or near the normal activation site which produces a fibrinolytically active form of t-PA. Activation of such a protein is expected to be specific for the clot site, given that significant amounts of thrombin would be expected to be associated with thrombi or clots in vivo.

According to the present invention, it is preferred to produce these novel proteins through the use of recombinant DNA technology, using cDNA clones or genomic clones as starting materials. cDNA clones encoding t-PA are disclosed by, for example, Pennica et al. (*Nature* 301: 214-221, 1983) and Kaufman et al. (*Mol. Cell. Biol.* 5: 1750-1759, 1985). Urokinase cDNA is disclosed by Genentech (EP 92,182). Partial and full-length cDNAs encoding plasminogen has been described by Malinowski et al. (*Biochemistry* 23: 4243, 1984) "and Forsgren et al., FEBS LETT. 213: 254, 1987". cDNAs encoding modified forms of t-PA are disclosed in copending, U.S. patent application Ser. No. 822,005 and in GB Patent Application No. 2,173,804. It is preferred to use cDNA clones because, by employing a full-length cDNA as the starting material for producing the modified fibrinolytic agents of the present invention, introns are removed so that all exons encoding the native protein are present and correctly oriented with respect to one another. To modify the cDNA or genomic DNA so that it encodes a thrombin cleavage site, amino acid changes are introduced by site-specific mutagenesis using conventional methods (for example, see Zoller and Smith, DNA 3: 479-488, 1984) using a cloned cDNA fragment as template. If using genomic DNA, it will generally be necessary to "loop out" introns using standard mutagenesis procedures. Suitable DNA sequences can also be synthesized according to standard procedures, or the mutant activation site may be constructed from synthesized oligonucleotides and then joined to the remainder of the coding sequence. The reconstructed coding sequence or mutated cDNA or genomic DNA is then inserted into an expression vector. The mutant sequences may be expressed in various host cells, including cultured mammalian cells, yeast and other fungi, and bacteria. Cultured mammalian cells are preferred. A particularly preferred mammalian cell line is the BHK cell line tk⁻ts13 (Waechter and Basserga, *Proc. Natl. Acad. Sci. USA* 79: 1106-1110, 1982) (hereinafter referred to as "th⁻BHK cells"). Methods for expressing cloned genes in each of these hosts are well known in the art. Suitable expression vectors will comprise a promoter capable of directing the transcription of a foreign gene in a host cell and a terminator. For efficient expression, an enhancer may also be included.

In some instances it is preferred that expression vectors further comprise an origin of replication, as well as sequences which regulate and/or enhance expression levels, depending on the host cell selected. Suitable expression vectors may be derived from plasmids, RNA and DNA viruses or cellular DNA sequences, or may contain elements of each. Selection of the necessary sequences and their assembly into an expression vector are well within the level of ordinary skill in the art.

Preferred prokaryotic hosts for use in carrying out the present invention are strains of the bacteria *Escherichia coli*, although Bacillus and other genera are also useful. Techniques for transforming these hosts and expressing foreign DNA sequences cloned in them are well known in the art (see, for example, Maniatis et al., *Molecular Cloning: A Laboratory Manual*, Cold Spring Harbor Laboratory, 1982). Vectors used for expressing foreign DNA in bacterial hosts will generally contain a selectable marker, such as a gene for antibiotic resistance, and a promoter which functions in the host cell. Appropriate promoters include the trp (Nichols and Yanofsky, *Meth. in Enzymology* 101: 155, 1983), lac (Casadaban et al., *J. Bact.* 143: 971-980, 1980), TAC (Russell et al., *Gene* 20: 231-243, 1982), and phage λ promoter systems. Plasmids useful for transforming bacteria include pBR322 (Bolivar et al., *Gene* 2: 95-113, 1977), the pUC plasmids (Messing, *Meth. in Enzymology* 101: 20-77, 1983; and Vieira and Messing, *Gene* 19: 259-268, 1982), pCQV2 (Queen, *J. Mol. Appl. Genet.* 2: 1-10, 1983), and derivatives thereof.

Eukaryotic microorganisms, such as the yeast *Saccharomyces cerevisiae*, or filamentous fungi including Aspergillus, may also be used as host cells. Particularly preferred species of Aspergillus include *A. nidulans*, *A. niger*, *A. oryzae*, and *A. terreus*. Aspergillus species may be transformed according to known procedures, for example, that of Yelton, et al. (*Proc. Natl. Acad. Sci. USA* 81: 1740-1747, 1984). Techniques for transforming yeast are described by Beggs (*Nature* 275: 104-108, 1978). Expression vectors for use in yeast include YRp7 (Struhl et al., *Proc. Natl. Acad. Sci. USA* 76: 1035-1039, 1979), YEp13 (Broach et al., *Gene* 8: 121-133, 1979), pJDB248 and pJDB219 (Beggs, ibid.), and derivatives thereof. Such vectors will generally comprise a selectable marker, such as the nutritional marker TRP, which allows selection in a host strain carrying a trp1 mutation or may utilize an "essential" gene, such as tpi1, as a selectable marker (EP 171,142). Preferred promoters for use in yeast expression vectors include promoters from yeast glycolytic genes (Hitzeman et al., *J. Biol. Chem.* 255: 12073-12080, 1980, Kawasaki, U.S. Pat. No. 4,599,311), or alcohol dehydrogenase genes (Young et al., in: *Genetic Engineering of Microorganisms for Chemicals*, Hollaender et al., eds., p. 335, Plenum, New York, 1982; and Ammerer, *Meth. in Enzymology* 101: 192-201, 1983).

In order to facilitate purification of a heterologous protein produced in a yeast transformant and to obtain proper disulphide bond formation, a signal sequence from a yeast gene encoding a secreted protein may be substituted for the pre-pro sequence of the heterologous gene or cDNA. A particularly preferred signal sequence is the pre-pro region of the MFα1 gene (Kurjan and Herskowitz, *Cell* 30: 933-943, 1982).

Higher eukaryotic cells may also serve as host cells in carrying out the present invention. Cultured mammalian cells, such as the BHK, CHO, NS-1, SP2/0 and J558L cell lines, are preferred. Tk⁻BHK cells are a particularly preferred adherent cell line. Expression vectors for use in mammalian cells will comprise a promoter capable of directing the transcription of a foreign gene introduced into a mammalian cell. Particularly preferred promoters include the SV40 promoter (Subramani et al., *Mol. Cell Biol.* 1: 854-64, 1981), the MT-1 promoter (Palmiter et al., *Science* 222: 809-814, 1983), and the mouse kappa gene promoter (Bergman et al. *Proc. Natl. Acad. Sci. USA* 81: 7041-7045, 1984). Also contained in the expression vectors is a transcription terminator, located downstream of the insertion site for the DNA sequence to be expressed. A preferred terminator is the human growth hormone (hGH) gene terminator (DeNoto et al., *Nuc. Acids Res.* 9: 3719-3730, 1981). In addition, vectors will preferably contain enhancer sequences appropriate to the particular host cell line.

For expression of the fibrinolytic proteins described herein in cultured mammalian cells, expression vectors containing cloned DNA sequences are introduced into the cells by appropriate transfection techniques, such as calcium phosphate-mediated transfection (Graham and Van der Eb, *Virology* 52: 456-467, 1973; as modified by Wigler et al., Proc. Natl. Acad. Sci. USA 77: 3567–3570, 1980) or electroporation (Neumann et al., EMBO J. 1: 841–845, 1982). In a typical application of the calcium phosphate method, a DNA-calcium phosphate precipitate is formed, and this precipitate is applied to the cells in the presence of medium containing chloroquine (100 uM). The cells are incubated for four hours with the precipitate, followed by a two-minute, 15% glycerol shock. A portion of the cells take up the DNA and maintain it inside the cell for several days. A small fraction of the cells integrate the DNA into the genome of the host cell or maintain the DNA in non-chromosomal nuclear structures. These transfectants can be identified by cotransfection with a gene that confers a selectable phenotype (a selectable marker). Preferred selectable markers include the DHFR gene, which imparts cellular resistance to methotrexate (MTX), an inhibitor of nucleotide synthesis, or the bacterial neomycin resistance gene, which confers resistance to the drug G418. After the host cells have taken up the DNA, drug selection is applied to select for a population of cells that are expressing the selectable marker at levels high enough to confer resistance.

Coamplification as a means to increase expression levels can be accomplished by the addition of high concentrations of MTX to the culture medium at the time of the initial selection, or subsequently, by sequentially increasing the concentration of MTX in the medium, followed by repeated cloning by dilution of the drug-resistant cell lines. Variations in the ability to amplify relate both to the initial genomic configuration (i.e., extra-chromosomal vs. chromosomal) of the cotransfected DNA sequences as well as to the mechanism of amplification itself, in which variable amounts of DNA rearrangements can occur. This is noticed upon further amplification of clones previously shown to be stable. For this reason, it is necessary to clone by dilution after every amplification step. Cells which express the DHFR marker are then selected and screened for production of the fibrinolytic protein. Screening may be done by enzyme-linked immunosorbent assay (ELISA) or by biological activity assays.

The fibrinolytic proteins so produced are recovered from the cultured cells by removing the culture medium and fractionating it. A preferred method of fractionation is affinity chromatography using an appropriate antibody. Other conventional purification methods, such as ion-exchange chromatography, high-performance liquid chromatography or gel filtration, may also be used.

Since the regions of t-PA, u-PA, and plasminogen downstream (C-terminal) of the Arg at the cleavage site are part of the serine protease portion of the molecule, structural determinants downstream are probably required for serine protease activity and are not preferred targets for modification in redesigning the activation site. Accordingly, a preferred strategy for designing an optimal thrombin cleavage site introduces changes N-terminal to the Arg residue, although the substitution of leucine for lysine (277) of the native t-PA also results in retention of protease activity, and may also significantly alter the fit into an active site, since the native Lys residue is positively charged.

Other changes in the N-terminal region (relative to the activation site) were determined, in part, through an alignment of protein sequences known to be natural substrates for thrombin. These include the fibrinogen A- and B-chains, factor V, factor VIII, factor XIII, protein C, protein S and urokinase. Within the present invention, thrombin is highly specific for cleavage after Arg residues. In addition, there is apparently a high degree of specificity for the amino acid in the P2 position, this usually being proline and occasionally Leu, Val or Ile. There is also a preference for Ser at P1'. Further, there is a general tendency toward hydrophobic amino acids at positions P3, P4 and P5. The region including positions P6 through P11 may be made more acidic, with the inclusion of more than one Asp or Glu residue in this region. In the P2, P9, P11, P12 and P13 positions, a Phe residue may be provided. In addition, changes at the P2 position may be combined with a change to Phe at position P3 to further reduce susceptibility to cleavage by plasmin.

By way of example, comparison of the t-PA activation site with this alignment of thrombin cleavage sites shows that the t-PA sequence does not contain any of the common structural features found in thrombin cleavage sites. This is not surprising, since t-PA is not a natural substrate for thrombin. Even if one mutates the amino acid in position P2 to Pro, as in mutant pMH10 disclosed herein, the resulting molecule still does not have the acidic region at P6-P11, does not have a Phe around P12, and instead has a Cys at P12 which is disulfide bonded to the serine protease domain. The presence of this disulfide may represent significant steric interference to fitting into the active site of thrombin. In spite of these differences, it has been found that the pMH10 protein is cleaved by thrombin.

It is generally preferred that changes at amino acids other than P2 be made in combination with a substitution at the P2 position.

Again, by way of example, additional mutant t-PA molecules which have altered activation site sequences are constructed based on the above-described structural considerations. Particularly preferred modified t-PA sequences are shown in Table 1. In Table 1, amino acids are identified by the standard one letter codes; the space indicates the position of the activation site.

TABLE 1

| Molecule | Sequence |
| --- | --- |
| Native t-PA | CGLRQYSQPQFR IKGG |
| pMH10 | CGLRQYSQPQPR IKGG |
| JK1062 | CGLSDEEEQPQPR IKGG |
| JK1068 | CGLRQSYSEEEEQPQPR IKGG |
| JK1070 | CGLSFAARQYSQPQPR IKGG |

Note:
Underlined amino acids constitute insertions or alterations to the sequence Mutant JK1062 incorporates acidic residues at positions P6 through P10. Mutant JK1068 is intended to increase the spacing between the cleaved bond and the Cys residue found in native t-PA at P12. In this mutant, the additional amino acids, inserted to give the spacing effect, also introduce acidic residues in positions P6 through P10. Mutant JK1070 introduces a Phe residue in position P12.

In order to make these changes in the t-PA molecule, site-directed mutagenesis was used to place unique restriction sites for Afl II and Nhe I at amino acid positions 266 and 284, respectively. These sites can be introduced by base changes which do not alter the amino acid sequence in these regions. Following placement of these restriction sites in the native t-PA cDNA, this fragment is excised from the native t-PA sequence and replaced with synthetic oligonucleotides encoding the desired activation site sequence.

The resultant DNA sequences encoding proteins according to the present invention are inserted into a suitable expression vector, which in turn is inserted into appropriate host cells as outlined above. The method of insertion into the host cell is well known to depend upon the particular host cell chosen and will be evident to one skilled in the art.

The proteins of the present invention are analyzed for their capacity to serve as substrates for thrombin and/or plasmin. The rate of one-chain to two-chain conversion is monitored by exposing the protein to thrombin or plasmin and withdrawing aliquots of the reaction- over time. These aliquots are then analyzed for the generation of amidolytic activity with the substrate S-2444 (for t-PA and urokinase derivatives) or S-2251 (for plasminogen derivatives) and also for the appearance of the two-chain form by Western blot analysis. Measurement of the appearance of the two-chain form as a function of time permits calculation of the kinetic rate constant for cleavage of these proteins. Comparison of these rate constants to those for the native proteins is used to identify the proteins which are most rapidly activated by thrombin.

The following examples are offered by way of illustration, and not by way of limitation.

EXAMPLES

Example 1

Construction of a Full-Length t-PA Clone

The sequence of a human t-PA cDNA clone has been reported (Pennica et al., *Nature* 301: 214-221, 1983). The sequence encodes a pre-pro peptide of 32-35 amino acids followed by a 527-530 amino acid mature protein.

A cDNA clone comprising the coding sequence for mature t-PA was constructed using as starting material mRNA from the Bowes melanoma cell line (Rijken and Collen, *J. Biol. Chem.* 256: 7035-7041, 1981). This cDNA was then used to construct the plasmid pDR1296. *Escherichia coli* strain JM83 transformed with pDR1296 has been deposited with the American Type Culture Collection under Accession No. 53347.

Because the pre-pro sequence was not present in the cDNA clone pDR1296, it was constructed from synthesized oligonucleotides and subsequently joined to the cDNA. The sequence of the resultant full-length clone is shown in FIG. 1. In the synthesized t-PA pre-pro sequence, cleavage sites for Bam HI and Nco I were introduced immediately 5' to the first codon (ATG) of the pre-pro sequence, and a Bgl II (Sau 3A, Xho II) site was maintained at the 3' end of the pre-pro sequence. The naturally-occurring pre-pro sequence lacks a convenient restriction site near the middle; however, the sequence GGAGCA (coding for amino acids −20 and −19, Gly-Ala) can be altered to GGCGCC to provide a Nar I site without changing the amino acid sequence.

To construct the pre-pro sequence, the following oligonucleotides were synthesized using an Applied Biosystems Model 380-A DNA synthesizer:

ZC131: 5'GGA TCC ATG GAT GCA ATG AAG AGA GGG CTC TGC TGT GTG3'

ZC132: 5'TGG CGC CAC ACA GCA GCA GCA CAC AGC AGAG3'

ZC133: 5'GGC GCC GTC TTC GTT TCG CCC AGC CAG GAA ATC CATG3'

ZC134: 5'AGA TCT GGC TCC TCT TCT GAA TCG GGC ATG GAT TTC CT3'

Following purification, oligomers ZC131 and ZC132 were annealed to produce an overlap of 12 base pairs (Section 1). Oligomers ZC133 and ZC134 were similarly annealed (Section 2).

The oligomers were mixed in Pol I buffer (Bethesda Research Labs), heated to 65° C. for five minutes, and slowly cooled to room temperature for four hours to anneal. Ten units of DNA polymerase I were added and the reaction proceeded for two hours at room temperature. The mixtures were electrophoresed on an 8% polyacrylamide-urea sequencing gel at 1,000 volts for 2½ hours in order to size fractionate the reaction products. The correct size fragments (those in which the polymerase reaction went to completion) were cut from the gel and extracted.

After annealing, Section 1 was cut with Bam HI and Nar I and cloned into Bam HI+Nar I−cut pUC8 (Vieira and Messing, *Gene* 19: 259-268, 1982; and Messing, *Meth. in Enzymology* 101: 20-77, 1983). Section 2 was reannealed and cut with Nar I and Bgl II and cloned into Bam HI+Nar I (Sau 3A, Xho I)−cut pUC8. Colonies were screened with the appropriate labeled oligonucleotides. Plasmids identified as positive by colony hybridization were sequenced to verify that the correct sequence had been cloned.

Section 1 was then purified from a Bam HI+Nar I double digest of the appropriate pUC clone. Section 2 was purified from a Nar I+Xho II digest. The two fragments were joined at the Nar I site and cloned into Bam HI−cut pUC8.

The t-PA sequence of pDR1296 was then joined to the synthesized pre-pro sequence in the following manner (FIG. 2). Plasmid pIC19R (Marsh et al., *Gene* 32: 481-486, 1984) was digested with Sma I and Hind III. The ori region of SV40 from map position 270 (Pvu II) to position 5171 (Hind III) was then ligated to the linearized pIC19R to produce plasmid Zem67. This plasmid was then cleaved with Bgl II and the terminator region from the human growth hormone gene (De Noto et al., *Nuc. Acids Res.* 9: 3719-3730, 1981) was inserted as a Bgl II-Bam HI fragment to produce plasmid Zem86. The synthesized t-PA pre-pro sequence was removed from the pUC8 vector by digestion with Sau 3A. This fragment was inserted into Bgl II-digested Zem86 to produce plasmid Zem88. Plasmid pDR1296 was digested with Bgl II and Bam HI and the t-PA cDNA fragment was isolated and inserted into Bgl II - cut Zem88. The resultant plasmid was designated "Zem94."

The vector, Zem99, comprising the MT-1 promoter, the complete t-PA coding sequence, and the hGH terminator, was then assembled in the following manner (FIG. 2). A Kpn I-Bam HI fragment comprising the MT-1 promoter was isolated from MThGH111 (Palmiter et al., *Science* 222: 809-814, 1983) and inserted into pUC18 to construct Zem93. Plasmid MThGH112 (Palmiter et al., ibid.) was digested with Bgl II and re-ligated to eliminate the hGH coding sequence. The MT-1 promoter and hGH terminator were then isolated as an Eco RI fragment and inserted into pUC13 to construct Zem4. Zem93 was then linearized by digestion with Bam HI and Sal I. Zem4 was digested with Bgl II and Sal I, and the hGH terminator was purified. The t-PA pre-pro sequence was removed from the pUC8 vector as a Bam HI-Xho II fragment. The three DNA fragments were then joined, and a plasmid having the structure of Zem97 (FIG. 2) was selected. Zem97 was cut with Bgl II, and the Xho 11 t-PA fragment from Zem94 was inserted. The resultant vector was designated "Zem99."

Example 2

Construction of pMH10

The mutant t-PA designated "pMH10" contains a proline in the P2 position. The coding sequence was derived from the native t-PA sequence by site-specific mutagenesis. A 472 bp Eco RI fragment comprising the t-PA sequence from bp 802 to bp 1274 was isolated from Zem99 and cloned into the Eco RI site of M13mp18 (replicative form). The recombinant phage were transfected into *E. coli* (JM101), and anti-sense strand DNA was isolated.

Site-specific mutagenesis was then carried out on the single-stranded, anti-sense template DNA using the mutagenic primer ZC620 (5'CAG CCT CAG CCT CGC ATC AA3') and a universal second primer (5'TCC CAG TCA CGA CTG3'). Twenty pmoles phosphorylated mutagenic primer and 20 pmoles second primer were combined with 1 pmole single-stranded template in 10 ul of 20 mM Tris, pH 7.5, 10 mM $MgCl_2$, 50 mM NaCl, 1 mM DTT and incubated at 65° C. for ten minutes, then five minutes at room temperature, and placed on ice. Ten ul of 20 mM Tris, pH 7.5, 10 mM $MgCl_2$, 2 mM ATP, 10 mM DTT containing 1 mM dNTPs, 2.5 units Klenow polymerase, and 3.5 units DNA ligase were added to the annealed DNA and the mixture incubated three hours at 15° C. The DNA was then transfected into competent *E. coli* JM101, and the cells were plated on YT agar and incubated at 37° C. Plaques were transferred to nitrocellulose and prehybridized at the Tm-4° C. of the mutagenic primer for one hour in 6x SSC, 10x Denhardt's and hybridized to $^{32}$P-labeled mutagenic primer at Tm-4° C. in the same solution. After three washes at Tm-4° C., filters were exposed to X-ray film overnight. Additional wash steps were performed at 5° C. higher increments as necessary to identify mutant plaques. The mutated inserts were sequenced by the dideoxy method.

Figure 3:
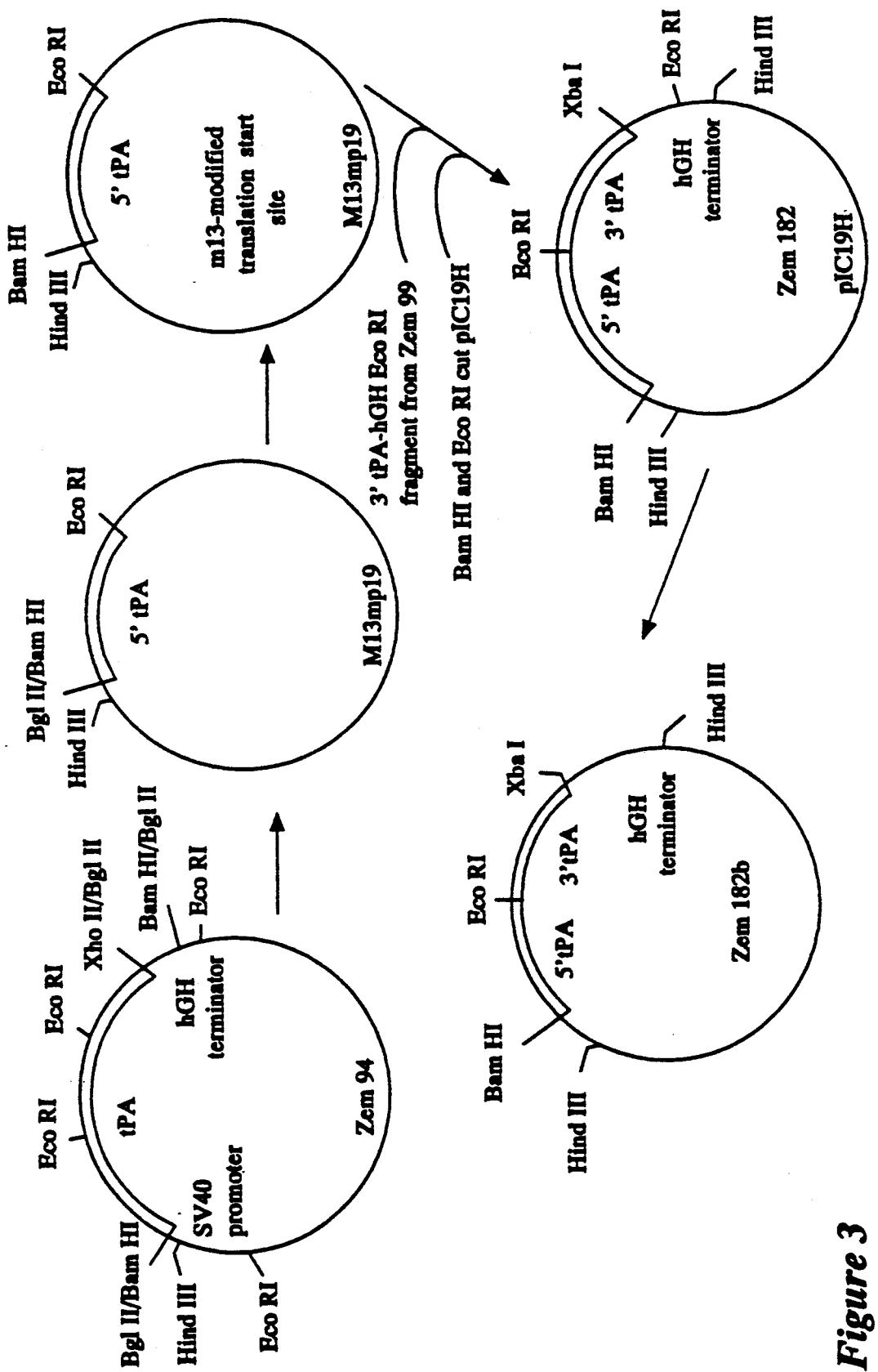
FIG. 3 illustrates the construction of the plasmid Zem182b.
Figure 4:
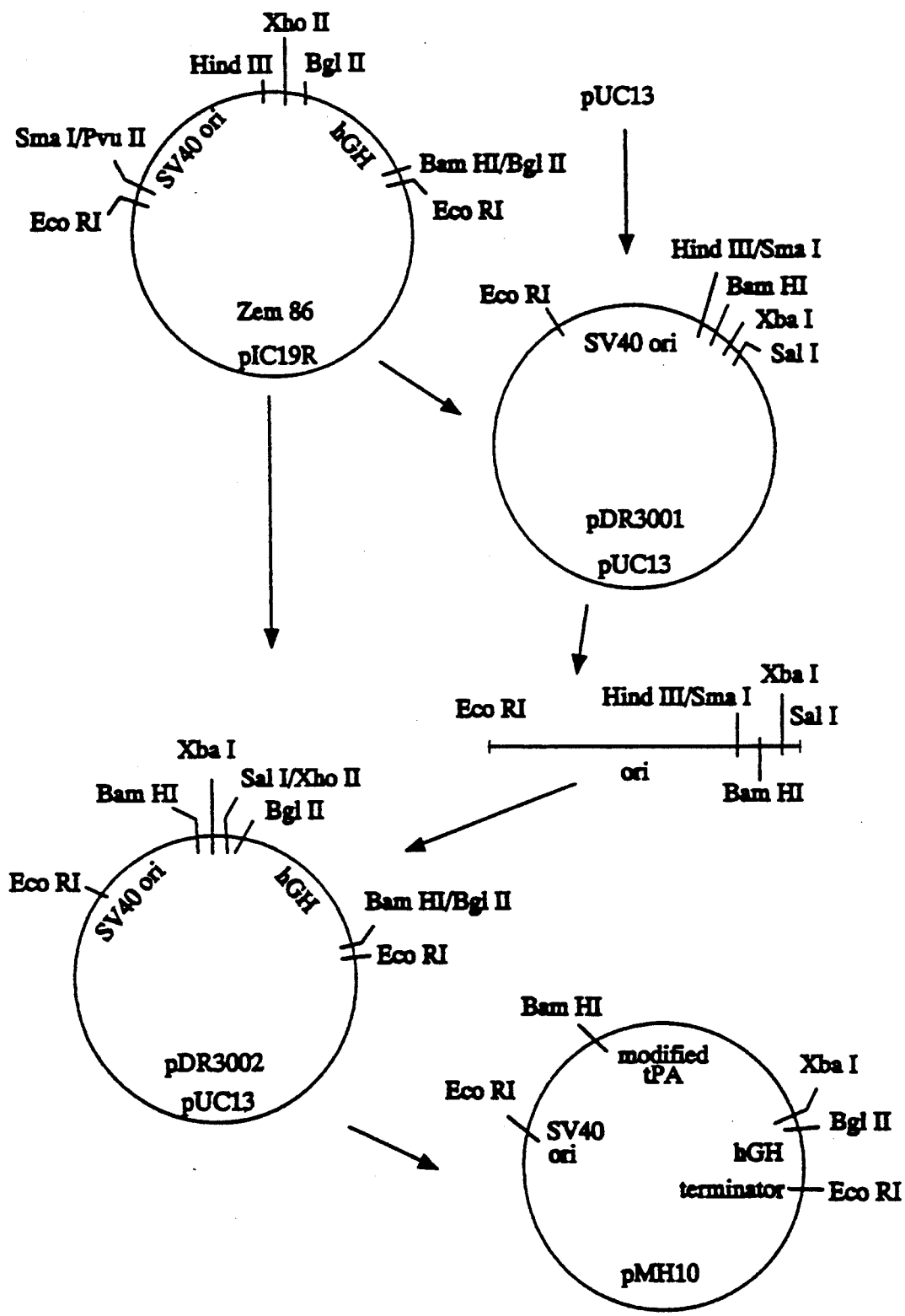
FIG. 4 illustrates the construction of plasmid pDR3002 and the expression vector pMH10.

An expression vector for the altered sequence was then constructed (FIGS. 3 and 4). The sequence just upstream of the ATG start codon of the t-PA sequence in Zem94 was altered by site-specific mutagenesis, resulting in the positioning of Hind III and Bam HI sites adjacent to the ATG. The resultant nucleotide sequence contains an adenine in the −3 position. Single-stranded M13 template DNA was prepared by inserting a ~800 bp Hind III-Eco RI fragment from Zem94, comprising polylinker, pre-pro, and a portion of the mature t-PA sequences, into M13mp19. Site-specific mutagenesis was carried out essentially as described above using the oligonucleotide ZC444 (5'CAT CCA TGG TGG ATC CAA GCT TGG C3') as mutagenic primer. The mutated inserts were sequenced by the dideoxy method, and a clone was selected in which polylinker sequences had been deleted and the Bam HI site at the 5' end of the pre-pro sequence had been restored. This phage clone was digested with Bam HI and Eco RI, and the 5' t-PA sequence was isolated. Zem99 was digested with Eco RI, and the fragment comprising the 3' portion of the t-PA sequence and the hGH terminator was isolated. The two fragments were then joined with Bam HI+Eco RI-digested pIC19H (Marsh et al., *Gene* 32: 481-486, 1984) in a three-part ligation. A plasmid containing the t-PA fragments in the proper orientation was selected and designated "Zem182." Plasmid Zem182 was partially digested with Eco RI, and the ends were filled using DNA polymerase I (Klenow fragment). The fragment was gel-purified and recirculared using $T_4$ DNA ligase. A plasmid in which the Eco RI site at the 3' end of the hGH terminator was destroyed was selected and designated "Zem182b."

The vector pDR3002 was used for expression of the above-described sequences. Plasmid Zem86 (described in Example 1) was digested with Hind III and the ends filled in using DNA polymerase I (Klenow fragment). The linearized DNA was then digested with Eco RI; and a $^{18}$ 350 bp fragment, comprising the SV40 ori sequence, was gel-purified and ligated to Sma I+Eco RI-digested pUC13. The resultant vector was designated "pDR3001." Plasmid pDR3001 was digested with Sal I and Eco RI; and the ~350 bp fragment, comprising SV40 ori and polylinker sequences, was gel-purified. Zem86 was partially digested with Eco RI and completely digested with Xho I to remove the SV40 ori sequence. The SV40 fragment from pDR3001 was then joined to the linearized Zem86. The resultant plasmid was designated pDR3002 (FIG. 4).

Replicative form (RF) DNA was prepared from the mutagenized phage, and the modified t-PA sequence was purified as an Eco RI fragment. Plasmid Zem182b was digested with Eco RI; and the large fragment, comprising the vector sequences and the 5' and 3' portions of the t-PA coding sequence, was selected. This fragment was treated with calf alkaline phosphatase, and the modified t-PA sequence was inserted. The resultant plasmid was digested with Bam HI and Xba I, and the t-PA fragment was inserted into Bam HI+Xba I−cut pDR3002. The resultant vector was designated "pMH10."

Example 3

Construction of JK4002 and Insertion of Oligonucleotides to Create Thrombin-Cleavable Mutants In order to facilitate construction of a large number of different thrombin-activated t-PA mutants, two unique restriction sites were introduced into the t-PA cDNA sequence without causing any changes in the encoded amino acid sequence. These two sites were introduced by site-specific mutagenesis in a similar manner to that described in Example 2. A 472 bp Eco RI fragment of the t-PA cDNA was subcloned into M13mp18. The oligonucleotides ZC989 (5'CTG CGG CTT AAG ACA GTA C3') and ZC1020 (5'CGA CAT CGC TAG CCA CCC CT3') were annealed simultaneously together with the universal primer to insert Afl II and Nhe I sites, respectively, at positions 267 and 285 of the t-PA amino acid sequence. A plaque which hybridized with both of the mutagenic oligonucleotides was sequenced to confirm the DNA changes and the presence of both mutations.

Following the mutagenesis, RF DNA was prepared from this plaque and the 472 bp Eco RI fragment was ligated into Eco RI - cut plasmid Zem182b. Colonies from this ligation with the correct orientation of the Eco RI fragment with respect to the rest of the t-PA cDNA were identified. The t-PA cDNA from this construction was digested with Bam HI and Xba I, and the t-PA fragment was purified from an agarose gel and ligated in the plasmid pDR3002, which had been cut with Bam HI and Xba 1. The resulting plasmid was designated "JK4002."

JK4002 was cut with Afl II and Nhe I, and the large fragment from this digestion was purified on an agarose gel. To make the thrombin site mutants, pairs of oligonucleotides encoding different sequences for the region from amino acids 267 to 285 were ligated to this fragment. The first set of oligonucleotides, ZC1060 and ZC1061 (Table 2), were constructed so that a new, unique Sst II restriction site was created at amino acid 275. This site allowed subsequent mutations to be created with oligonucleotide pairs which encoded either the region from amino acid 267 to 275 or from 275 to 285. The plasmid which contained the ZC1060/1061 pair was called "JK1060."

Pairs of oligonucleotides encoding sequences from amino acid 267 to 275 were ligated to the Afl II - Sst II-digested JK1060 to generate additional mutants. Following ligation, colonies which hybridized to the inserted oligonucleotide pairs were isolated and DNA was prepared from the colonies. The 472 bp Eco RI fragment was isolated from these DNAs and subcloned into M13 phage vectors for DNA sequence verification of the inserted sequence. Exemplary vectors and the oligonucleotides used to generate them are shown in Table 2. The amino acid sequences around the cleavage sites of the encoded mutant proteins are given in Table 1.

Example 4
Thrombin-Activated t-PA Mutant Lacking a Growth Factor Domain

A mutant sequence lacking the growth factor domain coding sequence was constructed by deletion mutagenesis using oligonucleotide ZC820 (5'GTA GCA CGT GGC CCT GGT TTT GAC AGG CAC TGA GTG3') and an M13 phage template containing the 5' Bam HI-Eco RI t-PA fragment. This deletion joined the codons for amino acids 49 and 88 of mature t-PA (FIG. 4D). A correct clone was identified by sequencing; however, the Bam HI site had been destroyed so the RF DNA was digested with Pvu II and Hind III. A 713 bp fragment comprising the mutated t-PA sequence was isolated and ligated to Sma I and Hind III - cut pUC18. The ligation mixture was transformed into E. coli HB101. A correct clone was identified and designated "pUC18-820."

Plasmid pUC18-820 was digested with Bgl II and Eco RI, and the modified t-PA sequence was purified. This fragment was ligated together with the 472 bp Eco RI internal t-PA fragment from Zem99 and with purified Zem182b vector DNA (Example 2 and FIG. 3) after digestion with Bgl II and Eco RI to remove wild-type t-PA sequences. The resultant plasmid was digested with Bam HI and Xba I and inserted into vector pDR3002 (Example 2 and FIG. 4) to make plasmid p820 (shown in FIG. 5). The protein encoded by this vector was designated "820."

Figure 5:
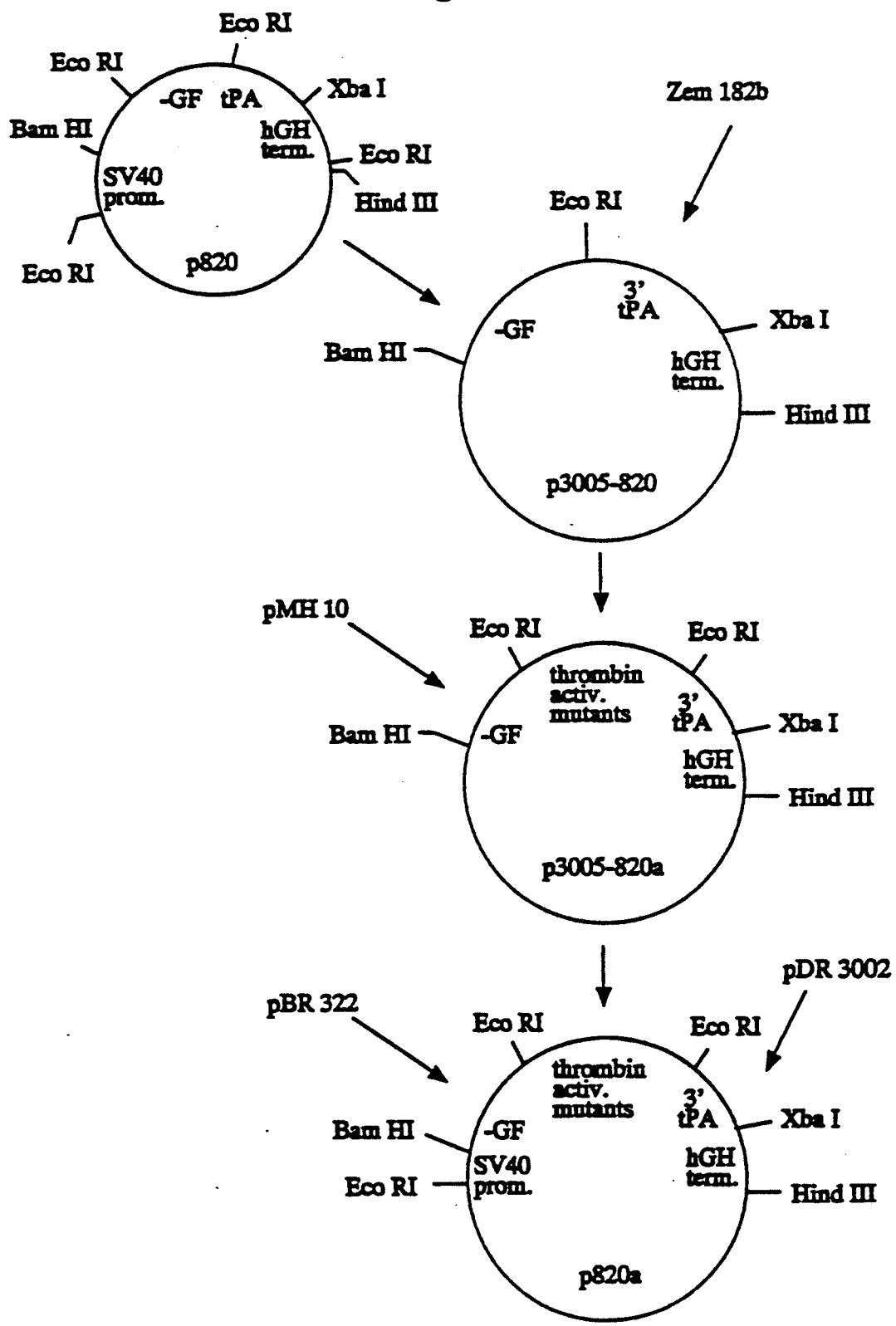

The internal Eco RI fragment from pMH10 was then combined with the Bam HI to Eco RI (−GF) 5' sequence and the Eco RI to Xba I 3' coding sequence for t-PA (FIG. 5). Plasmid p820 was digested with Bam HI and Eco RI, and the 5' -GF t-PA fragment was isolated. Plasmid Zem182b was digesting with Bam HI and Eco RI, and the large fragment, comprising the vector sequences and the 3' t-PA sequence, was isolated and ligated to the 5' Bam HI to Eco RI t-PA fragment. The resultant plasmid was designated "p3005-820." This plasmid was then linearized by digestion with Eco RI, and the 472 bp Eco RI fragment from pMH10 was

TABLE 2

| Vector | Oligonucleotides |
|---|---|
| JK1060 | ZC1060 5'TTA AGA CAG TAC AGC CAG GTG CAG CCG CGG ATC AAA GGA GGG CTC TTC GCC GAC ATC G3' |
| | ZC1061 5'CTG TCA TGT CGG TCC ACG TCG GCG CCT AGT TTC CTC CCG AGA AGC GGC TGT AGC GATC3' |
| JK1062 | ZC1062 5'TTA AGC GAT GAA GAA GAA CAG CCT CAG CCG C3' |
| | ZC1063 5'CG CTA CTT CTT CTT GTC GGA GTC GG3' |
| JK1068 | ZC1068 5'TTA AGA CAG TAC AGC GAA GAA GAA GAA CAG CCT CAG CCG C3' |
| | ZC1069 5'CT GTC ATG TCG CTT CTT CTT CTT GTC GGA GTC GG3' |
| JK1070 | ZC1070 5'TTA AGT TTC GCT GCT AGA CAG TAC AGC CAG CCT CAG CCG C3' |
| | ZC1071 5'CAA AGG GAC GAT CTG TCA TGT CGG TCG GAG TCG G3' | inserted to reconstruct the complete coding sequence. The resultant plasmid was designated "p3005-820a."

For expression vector construction, p3005-820a was digested with Bam HI and Xba I, and the mutant t-PA sequence was isolated. This fragment was inserted into Bam HI, Xba I - cut pDR3002 to produce the expression vector p820a.

In a similar manner, the altered cleavage sites of the plasmids JK1062, JK1068 and JK1070 are substituted for the native cleavage site of p820.

Figure 6:
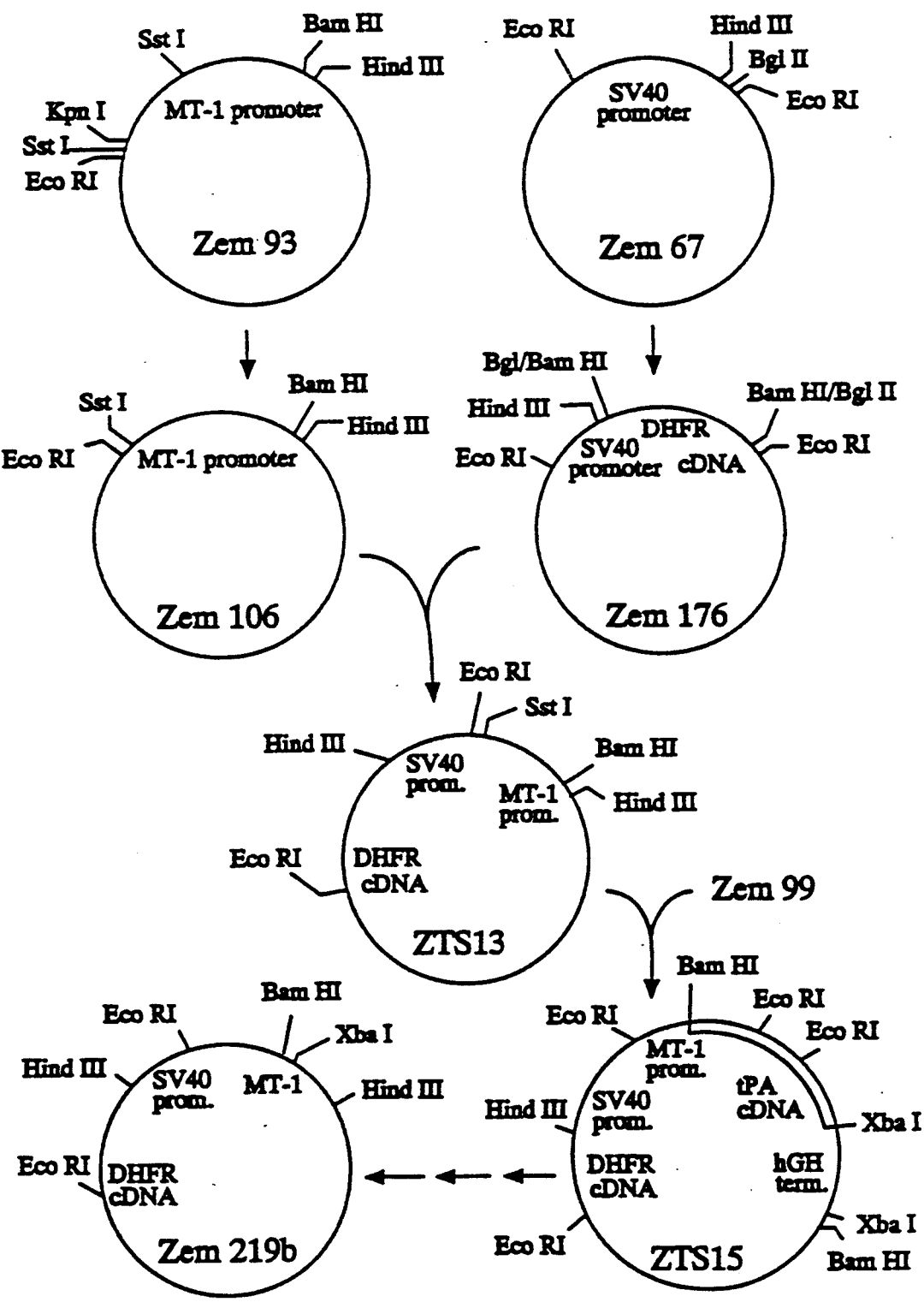
FIG. 6 illustrates the construction of the vector Zem219b.

An expression vector for the mutant sequences was constructed (FIG. 6). Plasmid pSV2-DHFR (Subramani et al., ibid.) was digested with Cfo I, and the fragment containing the DHFR cDNA and the 3' attached SV40 sequences was isolated, repaired, and ligated to Bam HI linkers. After digestion with Bam HI, an approximately 800 bp fragment containing the entire cDNA and the SV40 terminator region was purified and ligated to Bam HI-digested pUC8. Plasmid Zem67 was digested with Bgl II and ligated with the Bam HI DHFR-SV40 fragment to generate plasmid Zem176. Plasmid Zem93 was digested with Sst I and re-ligated to generate plasmid Zem106, in which approximately 600 bp of sequence 5' to the MT-1 promoter were eliminated. Plasmid Zem106 was digested with Eco RI and ligated to the Eco RI fragment containing the DHFR gene from Zem176. The resulting plasmid was designated "Zts13." Plasmid Zts13 was digested with Bam HI and ligated to the Bam HI fragment from plasmid Zem99, containing the entire native t-PA coding region and hGH terminator sequence, to generate plasmid Zts15. Zts15 was partially digested with Bam HI, repaired, and re-ligated to generate plasmid Zem219, in which the 3' Bam HI site was destroyed. Plasmid Zem219 was partially digested with Xba I, repaired, and re-ligated to generate plasmid Zem219a, in which the 3' Xba I site was destroyed. Plasmid Zem219a was digested with Bam HI and Xba I, the vector sequences were purified away from the t-PA sequences, and the vector portion was ligated with an oligomeric Bam HI-Xba I adaptor to generate the expression vector Zem219b (FIG. 6).

The resultant mutant coding sequences are inserted into Bam HI, Xba I-digested Zem219b (FIG. 6) to construct expression vectors p820d-f.

Expression vectors are transfected into tk$^-$BHK cells by an electroporation transfection protocol. High-producing transfected cell lines are selected and scaled up for production and characterization of the mutant proteins.

Example 5

Thrombin-Activated t-PA Mutants Lacking Carbohydrate Addition Site on $K_1$ Domain Native t-PA contains four potential N-linked glycosylation sites (amino acid sequence Asn-X-Ser/Thr), three of which have been reported to be glycosylated in t-PA obtained from Bowes melanoma cells (Pohl et al., Biochemistry 23: 3701-3707, 1984). By altering the Asn residues (preferably to Gln) at the glycosylation sites through site-specific mutagenesis of the cDNA, carbohydrate addition is blocked.

A mutant t-PA sequence encoding a thrombin-activated protein lacking both the GF domain and carbohydrate at position 117 in the $K_1$ domain was constructed. Plasmid p820 was digested with Bam HI and Eco RI, and the 614 bp fragment was isolated and cloned into Bam HI, Eco RI-digested M13mp18 (RF).

Site-specific mutagenesis was performed using the mutagenic primer ZC326 (5'ACC AAC TGG CAA TCT AGC GCG TTG3'). A correctly mutated clone was identified by dideoxy DNA sequencing. RF DNA was isolated from a sequenced clone and digested with Bam HI and Eco RI, and the mutated t-PA sequence was isolated. The complete coding sequence for the mutant protein was then assembled in an expression vector by combining the mutant Bam HI-Eco RI fragment, the 1010 bp partial Eco RI-Xba I fragment from pMH10, and the large (vector) fragment from a Bam HI+Xba I digest of Zem219b. The resultant vector was designated "p820c."

A second mutant sequence encoding a thrombin-activated t-PA variant lacking the finger and growth factor domains and lacking the carbohydrate addition site at position 117 in the Kringle 1 domain was constructed.

The strategy for deleting the finger and growth factor sequences used as starting material the plasmid pDR1496, which comprises the t-PA coding sequence. S. cerevisiae strain E8-11C transformed with pDR1496 has been deposited with the American Type Culture Collection under Accession No. 20728. To prepare a template for mutagenesis of the t-PA sequence, 1 μg of pDR1496 was digested with 5 units each of Sph I and Xba I for 2 hours at 37° C. The DNA was electrophoresed on a 0.7% agarose gel and a fragment of ~2100 bp was purified. This fragment was ligated to Sph I+Xba I-digested M13tg130 (replicative form; obtained from Amersham; Kieny et al., Gene 26: 91, 1983) to construct M13tg130W. The recombinant phage were transfected into E. coli JM103 and single-stranded template DNA was prepared. Oligonucleotide-directed deletion mutagenesis was carried out using 20 pmoles phosphorylated mutagenic primer (sequence: 5'CGT GGC CCT GGT ATC TTG GTA AG3') and 1 pmole template DNA in 20 mM Tris pH 7.5, 10 mM MgCl$_2$, 50 mM NaCl, 1 mM DTT at 65° C. for 10 minutes. The mixture was then incubated for 5 minutes at room temperature and placed on ice. Ten μl of 20 mM Tris pH 7.5, 10 mM MgCl$_2$, 2 mM ATP, 10 mM DTT containing 1 mM dNTPs, 2.5 units Klenow fragment and 3.5 units T$_4$ DNA ligase were added and the annealed DNA mixture was incubated for 3 hours at 15° C. The DNA was transfected into E. coli JM103, and the cells were plated on YT agar and incubated at 37° C. Plaques were screened to identify mutant plaques. A mutant sequence having the desired deletion of finger and growth factor sequences was designated "clone #2600."

DNA from deletion mutant 2600 was digested with Bam HI and Eco RI. The 473 bp Bam HI-Eco RI DNA fragment was isolated and cloned into the Bam HI and Eco RI sites of M13mp18. Site-specific mutagenesis was performed according to standard methods using the mutagenic primer ZC326. Correctly mutagenized phage clones were identified by dideoxy DNA sequencing. One correctly mutated clone was sequenced throughout the entire insert to ensure integrity of the fragment. RF DNA was prepared from the sequenced clone and digested with Bam HI and Eco RI. The correct size Bam HI to Eco RI fragment was isolated. The final expression vector, designated "2600c," was constructed by a three-part ligation of Bam HI and Xba I - cut Zem219b, the 473 bp Bam HI-Eco RI-mutated fragment, and the 1010 bp Eco RI-Xba I fragment from pMH10.

Example 6 t-PA - Plasminogen Hybrid Protein Containing a Thrombin Activation Site

A hybrid DNA sequence was constructed which encoded a protein consisting of the entire amino-terminal portion of t-PA (up to the cysteine at position 261) joined to the serine protease domain of plasminogen beginning at amino acid 541 (just to the amino-terminal side of the normal activation site). This hybrid protein was designated "PAP."

An approximately 1800 bp cDNA encoding human plasminogen from amino acid 272 (Malinowski et al., Biochemistry 23: 4243, 1984) was isolated as a Pst I-Sph I fragment. This fragment was cloned into Pst I, Sph I-digested pUC118 and mutagenized using the oligonucleotide primer ZC724 having the sequence 5'CAG TGT GCG GTA CCT TCA TTT G3' to introduce a Kpn I site between the codons for amino acids 542 and 543. The mutagenesis also results in a valine codon at position 542. A clone (designated "pPlas") having the desired alteration was identified and digested with Kpn I and Sph I, and the fragment encoding the serine protease domain of plasminogen was isolated (FIG. 7).

To construct the hybrid sequence, plasmid pDR816 (comprising the entire native t-PA coding sequence from Zem99) was digested with Bam HI and Sca I, and the 5' t-PA sequence was isolated. This fragment was then joined to the plasminogen coding fragment by means of a linker constructed by annealing oligonucleotides ZC784 (5'ACT GTG ATG TGC CCT CCT GCG CGG TAC3') and ZC785 (5'CGC GCA GGA GGG CAC ATC ACA GT3'). The three fragments (5' t-PA, annealed linkers, and 3' plasminogen) were joined in a four-part ligation to Bam HI, Sph I - cut pUC118 to construct plasmid pPAP (FIG. 7). The hybrid DNA was sequenced by the dideoxy method. The verified DNA sequence and the encoded amino acid sequence are shown in FIG. 8.

Figure 7:
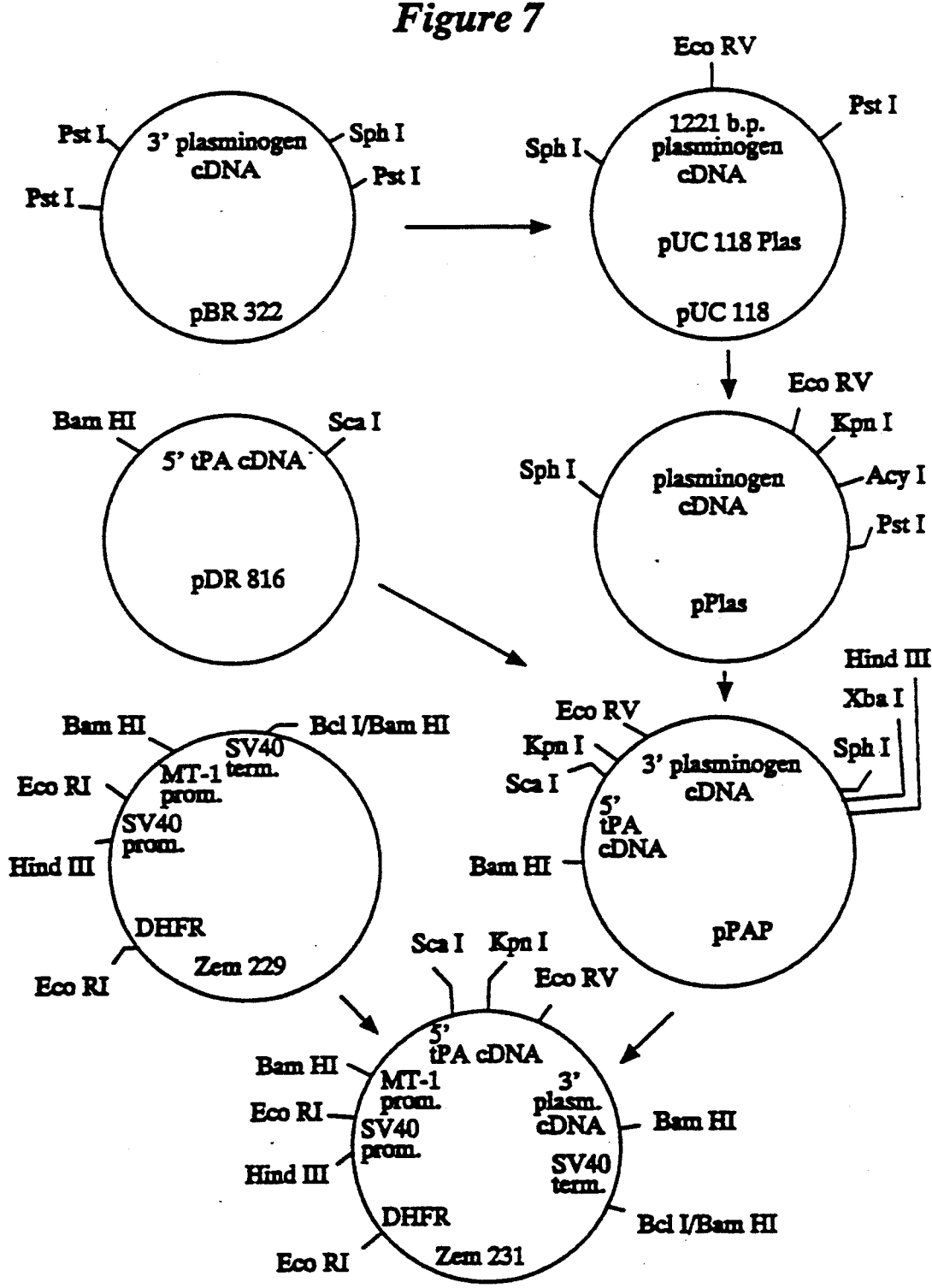
FIG. 7 illustrates the construction of a DNA sequence encoding a t-PA/plasminogen hybrid protein.

To introduce a thrombin-cleavable activation site into the t-PA-plasminogen hybrid sequence, plasmid pPAP was digested with Bam HI and the hybrid fragment was cloned into the plasmid Zem229, a plasmid consisting of the 237 bp Bcl I-Bam HI SV40 terminator from pSV2-DHFR inserted into Bam HI-digested Zts13 (FIG. 6), to generate plasmid Zem231 (FIG. 7). Zem231 thus contains both the PAP gene and the DHFR gene. The M13 template pPLAS was then mutated by site-specific mutagenesis to introduce thrombin-cleavable activation sites. Mutagenized sequences were isolated by digestion of RF DNA with Kpn I and Eco RV and were inserted into Zem231 which had been digested with Kpn I and Eco RV to eliminate the native activation site.

Example 7

Thrombin-Activated Plasminogen

A lambda phage clone comprising a cDNA sequence encoding plasminogen was obtained from Dr. Mark Martsen at the University of Washington. The cDNA was isolated from a human liver library by probing with the partial sequence of Malinowski et al. (ibid.). The sequence of the complete cDNA and the encoded amino acid sequence are shown in FIG. 10.

Figure 9:
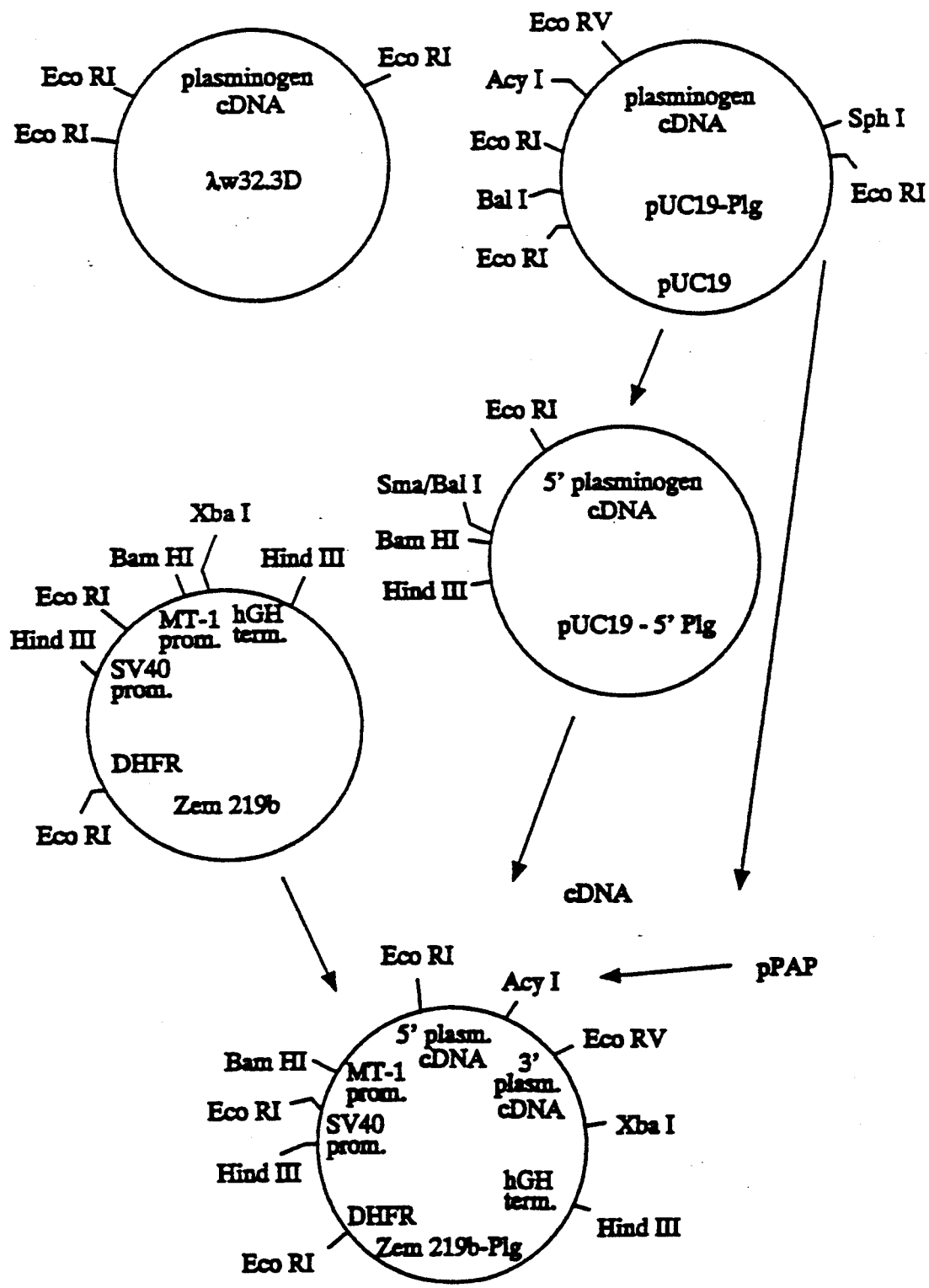
FIG. 9 illustrates the construction of a DNA sequence encoding a thrombin-activated plasminogen mutant.

Referring to FIG. 9, phage DNA was prepared by conventional procedures and subjected to partial digestion with Eco RI. A fragment of approximately 2800 bp, containing the entire plasminogen coding region, was isolated and cloned into pUC19 to construct pUC19-Plg. This plasmid was digested with Bal I and Eco RI, and the 5' plasminogen coding fragment was isolated and cloned into Sma I, Eco RI - cut pUC19. The resultant plasmid, designated "pUC19-5'Plg," was cut with Bam HI and Eco RI, and the 190 bp fragment was isolated. Plasmid pUC19-Plg was also digested with Eco RI and Eco RV, and the fragment comprising the middle portion of the cDNA was isolated. The fragment containing the 3' end of the plasminogen sequence was isolated from an Eco RV, Xba I digest of pPAP. The three plasminogen cDNA fragments were then ligated with Bam HI, Xba I-digested Zem219b to construct the vector Zem219b-Plg.

To insert a thrombin-cleavable activation site into the plasminogen sequence, plasmid Zem219b-Plg is digested with Acy I and Eco RV, and the vector plus cDNA sequences are purified away from the authentic activation site-coding fragment. The plasminogen sequence contained within the pPlas template (FIG. 7) is mutagenized according to conventional procedures, and the resultant activation region is inserted into the cleaved Zem219b-Plg.

Example 8

Expression, Purification and Characterization of Protein

Expression vectors pMH10, JK1062, JK1068 and JK1070 were transfected into tk-BHK cells by calcium phosphate co-precipitation with pSV2-DHFR (Subramani et al., ibid.), a plasmid carrying the gene for resistance to methotrexate (MTX). All other mutant vectors were transfected by electroporation. MTX-resistant colonies were isolated and tested for their production of t-PA-like polypeptide by enzyme-linked immunosorbent assay (ELISA).

Colonies which produced relatively high amounts of protein were expanded for large-scale culture. Spent media from large-scale culture which contained the mutant proteins were applied to an immuno-affinity column made from a monoclonal or polyclonal antibody to t-PA or plasminogen. The mutant proteins were eluted from the column with pH 11.5 buffer and immediately neutralized with 1M Tris, pH 7.5. The concentration of protein in the column eluate was determined by ELISA, and the samples were stored at $-20°$ C. until further analysis.

The mutant proteins and native t-PA were tested in a cleavage assay with plasmin and thrombin. The proteins were monitored for one- and two-chain forms by Western blotting, and rate constants for cleavage were determined. Data are presented in Table 3.

TABLE 3

| Protein | Rate Constant $[M^{-1}][sec^{-1}]$ | |
|---|---|---|
| | Plasmin | Thrombin |
| native t-PA | $4.7 \times 10^5$ | 0 |
| pMH10 | $1.8 \times 10^5$ | $7.1 \times 10^4$ |
| JK1062 | | $<10^4$ |
| JK1068 | | $<10^4$ |
| JK1070 | $2.0 \times 10^5$ | $1.3 \times 10^5$ |

Figure 11:
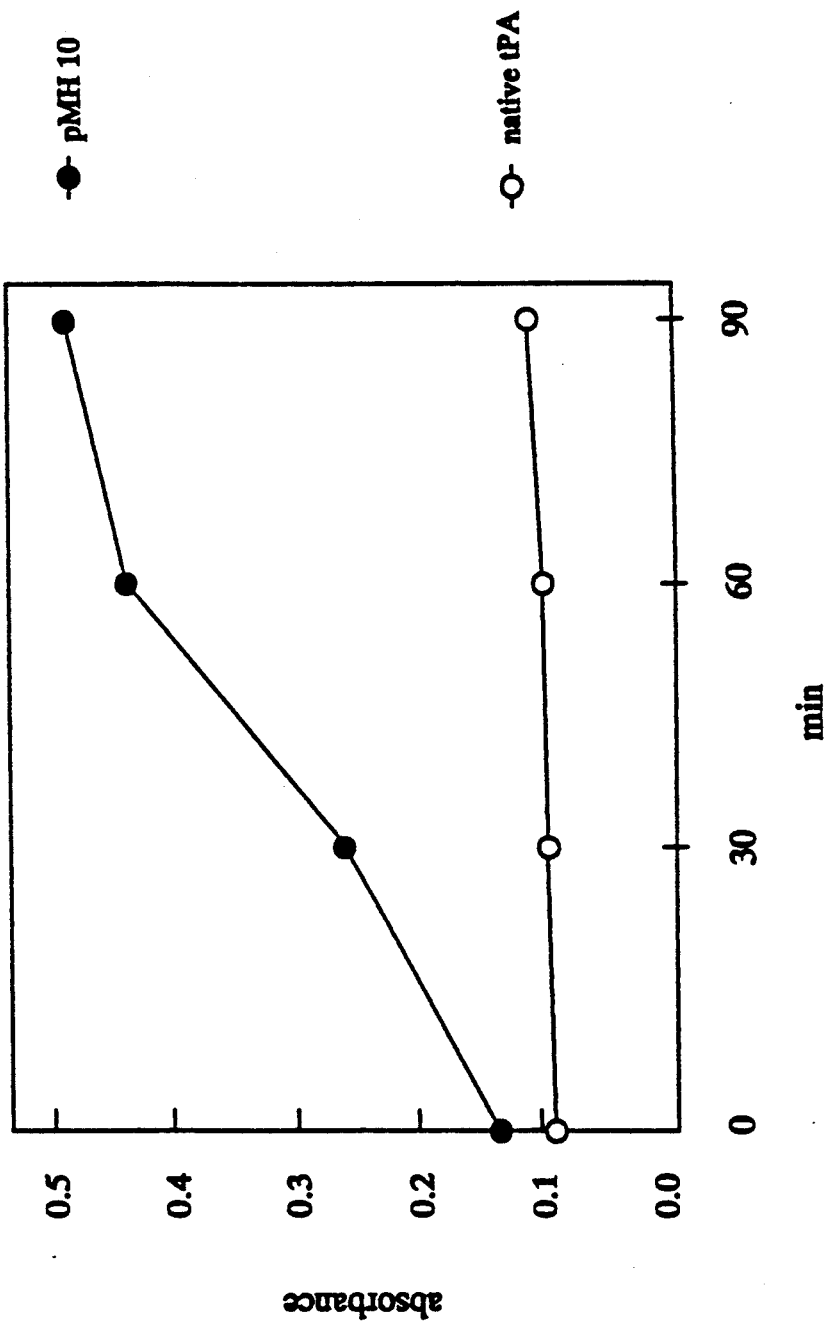
FIG. 11 illustrates the results of an amidolytic assay showing the activation of the pMH10 protein by thrombin.

The pMH10 protein and a control sample of recombinant native t-PA produced in BHK cells were incubated with catalytic amounts of bovine thrombin. Aliquots of the reaction mix were removed at different time intervals and assayed for t-PA amidolytic activity with the substrate S-2444. As shown in FIG. 11, the pMH10 protein is rapidly converted to an active form by incubation with thrombin, whereas no conversion of native t-PA is seen.

Figure 12:
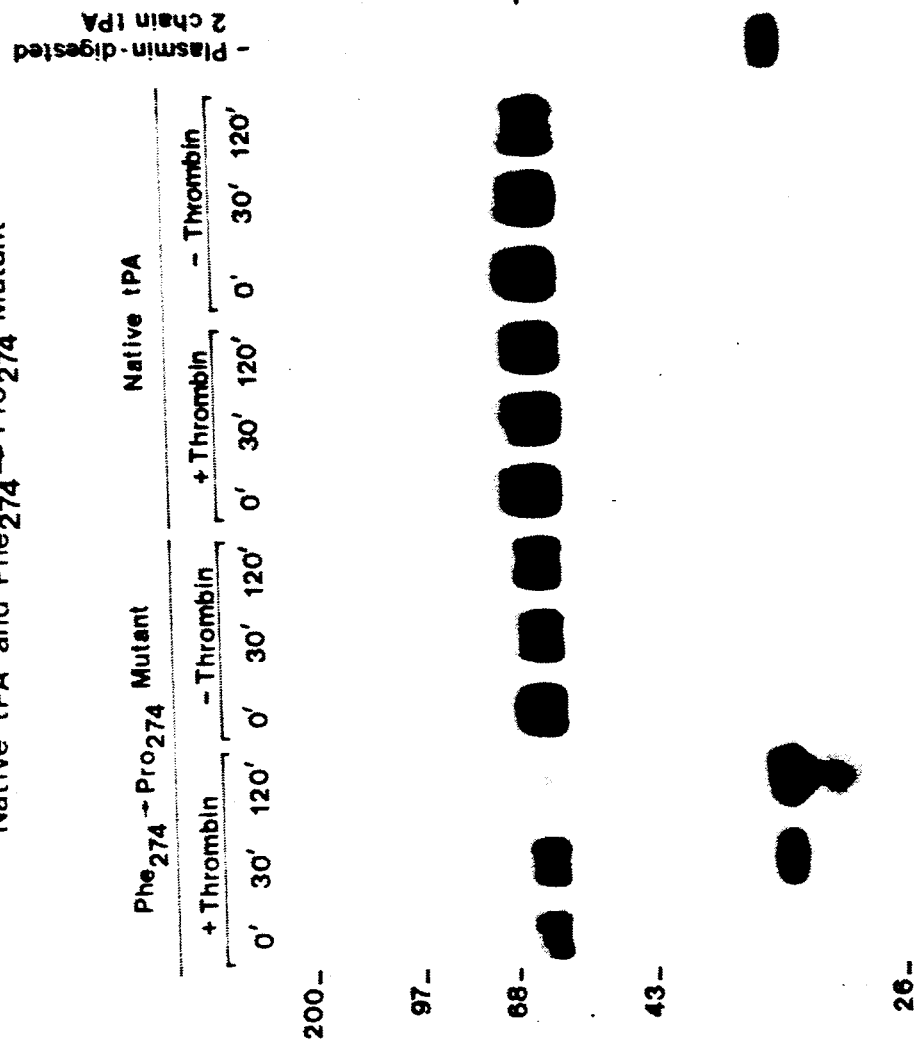
FIG. 12 shows a Western blot of native t-PA and pMH10 protein which had been incubated with bovine thrombin.

To demonstrate that cleavage by thrombin was responsible for the activation of the pMH10 protein, the activation reaction was repeated, and aliquots of each time point were analyzed on a Western blot (FIG. 12). The results clearly show the appearance of a two-chain form of pMH10 protein in the samples, coincident with the appearance of amidolytic activity. No two-chain form is seen in the pMH10 control without thrombin or in the native t-PA control with or without thrombin. Thus, there appears to be a specific cleavage of this protein by thrombin at or near the normal activation site, which cleavage results in the activation of the pMH10 protein.

The pMH10 protein was also analyzed for its ability to support plasminogen-dependent clot lysis in vitro. The clot lysis assay is designed to measure release of radiolabeled fibrinogen incorporated into the clot, following the addition of plasminogen and a t-PA sample. Results of this assay showed the pMH10 protein to be essentially equal to native t-PA in the rate of release of fibrinogen peptides from the clots as a function of incubation time.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A single chain form of a human t-PA, wherein said single chain form is cleavable by thrombin, said cleavage resulting in stimulation of amidolytic activity.

2. The single chain form of claim 1 wherein said single chain form contains an amino acid substituting at the P2 position.

3. The single chain form of claim 2 wherein the substituted amino acid at the P2 position is selected from the group consisting of proline, leucine, valine and isoleucine.

4. The single chain form of claim 2 wherein the substituted amino acid at the P2 position is proline.

5. A pharmaceutical composition comprising a single chain form of a human t-PA, wherein said single chain form is cleavable by thrombin, said cleavage resulting in stimulation of amidolytic activity, and a physiologically acceptable carrier or diluent.

6. The composition of claim 5 wherein said single chain form contains an amino acid substitution at the P2 position.

7. The composition of claim 6 wherein the substituted amino acid at the P2 position is selected from the group consisting of proline, leucine, valine and isoleucine.

8. The composition of claim 6 wherein the substituted amino acid at the P2 position is proline.

9. A DNA construct encoding a single chain form of a human t-PA, wherein said single chain form is cleavable by thrombin, said cleavage resulting in stimulation of amidolytic activity.

10. An expression vector containing a DNA construct encoding a single chain form of a human t-PA, wherein said single chain form is cleavable by thrombin, said cleavage resulting in stimulation of amidolytic activity.

11. Cells transfected or transformed with an expression vector containing a DNA construct encoding a single chain form of a human t-PA, wherein said single chain form is cleavable by thrombin, said cleavage resulting in stimulation of amidolytic activity.

* * * * *

UNITED STATES PATENT AND TRADEMARK OFFICE
CERTIFICATE OF CORRECTION

PATENT NO. :  5,200,340
DATED      :  April 6, 1993
INVENTOR(S):  Donald C. Foster et al.

It is certified that error appears in the above-identified patent and that said Letters Patent is hereby corrected as shown below:

In column 22, claim two, line five, please delete "substituting" and substitute therefor --substitution--.

In column 22, claim two, line six, please delete "P2position" and substitute therefor --P2 position--.

Signed and Sealed this

Eleventh Day of January, 1994

Attest:

BRUCE LEHMAN

Attesting Officer      Commissioner of Patents and Trademarks